United States Patent
Bennett et al.

(10) Patent No.: US 6,710,174 B2
(45) Date of Patent: Mar. 23, 2004

(54) ANTISENSE INHIBITION OF VASCULAR ENDOTHELIAL GROWTH FACTOR RECEPTOR-1 EXPRESSION

(75) Inventors: C. Frank Bennett, Carlsbad, CA (US); Andrew T. Watt, Vista, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 301 days.

(21) Appl. No.: 09/953,318

(22) Filed: Sep. 13, 2001

(65) Prior Publication Data

US 2003/0105036 A1 Jun. 5, 2003

(51) Int. Cl.$^7$ .............................. C07H 21/04
(52) U.S. Cl. .................. 536/24.5; 536/24.3; 536/24.31; 536/24.33
(58) Field of Search .................. 435/6, 91.1, 91.3, 435/325, 375; 536/23.1, 23.2, 24.3, 24.31, 24.33, 24.5; 514/44

(56) References Cited

U.S. PATENT DOCUMENTS

| | | | |
|---|---|---|---|
| 5,801,154 A | * | 9/1998 | Baracchini et al. |
| 5,830,880 A | | 11/1998 | Sedlacek et al. |
| 5,861,484 A | | 1/1999 | Kendall et al. |
| 5,916,763 A | | 6/1999 | Williams et al. |
| 5,994,076 A | * | 11/1999 | Chenchik et al. |

FOREIGN PATENT DOCUMENTS

| | | | |
|---|---|---|---|
| GB | WO 95/33050 | * | 12/1995 |
| WO | WO 97/15662 | * | 5/1997 |
| WO | WO 98/07851 | | 2/1998 |
| WO | WO 00/75319 | | 12/2000 |

OTHER PUBLICATIONS

Green et al, Antisense Oligonucleotides: An Evolving Technology for the Modulation of Gene Expression in Human Disease, Jul. 2000, Journal Amer. Coll. Surg., vol. 191, No. 1, pp. 93–105.*

Yu Jen, Suppression of Gene Expression by Targeted Disruption of Messenger RNA: Available Options and Current Stratgies, 2000, Stem Cells, vol. 18, pp. 307–319.*

Andrea D. Branch, A good antisense molecule is hard to find, Feb. 1998, Tibs, vol. 23, pp. 45–50.*

Bernatchez et al., *Vascular endothelial growth factor effect on endothelial cell proliferation, migration, and platelet–activating factor synthesis is Flk–1–dependent*, J. Biol. Chem., 1999, 274:31047–31054.

Clauss et al., *The vascular endothelial growth factor receptor Flt–1 mediates biological activities. Implications for a functional role of placenta growth factor in monocyte activation and chemotaxis*, J. Biol. Chem., 1996, 271:17629–17634.

Epstein et al., *Therapeutic interventions for enhancing collateral development by administration of growth factors: basic principles, early results and potential hazards*, Cardiovasc. Res., 2001, 49:532–542.

Fong et al., *Role of the Flt–1 receptor tyrosine kinase in regulating the assembly of vascular endothelium*, Nature, 1995, 376:66–70.

Fong et al., *Increased hemangioblast commitment, not vascular disorganization, is the primary defect in flt–1 knock–out mice*, Development, 1999, 126:3015–3025.

Goldman et al., *Paracrine expression of a native soluble vascular endothelial growth factor receptor inhibits tumor growth, metastasis, and mortality rate*, Proc. Natl. Acad. Sci. U.S.A., 1998, 95:8795–8800.

Graeven et al., *Melanoma–associated expression of vascular endothelial growth factor and its receptors FLT–1 and KDR*, J. Cancer Res. Clin. Oncol., 1999, 125:621–629.

Gunningham et al., *VEGF–B expression in human primary breast cancers is associated with lymph node metastasis but not angiogenesis*, J. Pathol., 2001, 193:325–332.

Gunningham et al., *Vascular encothelial growth factor–B and vascular endothelial growth factor–C dexpression in renal cell carcinomas: regulation by the von Hippel–Lindau gene and hypoxia*, Cancer Res., 2001, 61:3206–3211.

Hiratsuka et al., *Involvement of Flt–1 tyrosine kinase (vascular endothelial growth factor receptor–1) in pathological angiogenesis*, Cancer Res., 2001, 61:1207–1213.

Hornig et al., *Release and complex formation of soluble VEGFR–1 from endothelial cells and biological fluids*, Lab. Invest., 2000, 80:443–454.

Imbert et al., *Characterization of a yeast artificial chromosome from chromosomme band 13q12 containing the FLT1 and FLT3 receptor–type tyrosine kinase genes*, Cytogenet. Cell. Genet., 1994 67:175–177.

Kendall et al., *Identification of a natural soluble form of the vascular endothelial growth factor receptor, FLT–1, and its heterodimerization with KDR*, Biochem. Biophys. Res. Commun., 1996, 226:324–328.

Masood et al., *Vascular endothelial growth factor/vascular permeability factor is an autocrine growth factor for AIDS–Kaposi sarcoma*, Proc. Natl. Acad. Sci. U.S.A., 1997, 94:979–984.

(List continued on next page.)

Primary Examiner—Karen Lacourciere
(74) Attorney, Agent, or Firm—Licata & Tyrrell P.C.

(57) ABSTRACT

Antisense compounds, compositions and methods are provided for modulating the expression of vascular endothelial growth factor receptor-1. The compositions comprise antisense compounds, particularly antisense oligonucleotides, targeted to nucleic acids encoding vascular endothelial growth factor receptor-1. Methods of using these compounds for modulation of vascular endothelial growth factor receptor-1 expression and for treatment of diseases associated with expression of vascular endothelial growth factor receptor-1 are provided.

1 Claim, No Drawings

OTHER PUBLICATIONS

Matsuzaki et al., *Vascular endothelial growth factor rescues hippocampal neurons from glutamate–induced toxicity: signal transduction cascades,* Faseb J., 2001, 12:12.

Roeckl et al., *Differential binding characteristics and cellular inhibition by soluble VEGF receptors 1 and 2,* Exp. Cell Res., 1998, 241:161–170.

Shibuya, *Structure and dual function of vascular endothelial growth factor receptor–1 (Flt–1),* Int. J. Biochem. Cell Biol., 2001, 33:409–420.

Shibuya et al., *Nucleotide sequence and expression of a novel human receptor–type tyrosine kinase gene (flt) closely related to the fms family,* Oncogene, 1990, 5:519–524.

Wiesmann et al., *Crystal structure at 1.7 A resolution of VEGF in complex with domain 2 of the Flt–1 receptor,* Cell, 1997, 91:695–704.

Yamagishi et al., *Vascular endothelial growth factor acts as a pericyte mitogen under hypoxic conditions,* Lab. Invest., 1999, 79:501–509.

Zachary et al., *Signaling transduction mechanisms mediating biological actions of the vascular endothelial growth factor family,* Cardiovasc. Res., 2001, 49:568–581.

\* cited by examiner

SEQUENCE LISTING

<160> NUMBER OF SEQ ID NOS: 154

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                              20

<210> SEQ ID NO 3
<211> LENGTH: 7680
<212> TYPE: DNA
<213> ORGANISM: Homo sapiens
<220> FEATURE:
<221> NAME/KEY: CDS
<222> LOCATION: (250)...(4266)

<400> SEQUENCE: 3

```
gcggacactc ctctcggctc ctccccggca gcggcggcgg ctcggagcgg gctccggggc     60
tcgggtgcag cggccagcgg gcctggcggc gaggattacc cggggaagtg gttgtctcct    120
ggctggagcc gcgagacggg cgctcaggc gcggggccgg cggcggcgaa cgagaggacg    180
gactctggcg gccgggtcgt tggccggggg agcgcgggca ccgggcgagc aggccgcgtc    240 gcgctcacc atg gtc agc tac tgg gac acc ggg gtc ctg ctg tgc gcg ctg    291
          Met Val Ser Tyr Trp Asp Thr Gly Val Leu Leu Cys Ala Leu
            1               5                  10 ctc agc tgt ctg ctt ctc aca gga tct agt tca ggt tca aaa tta aaa    339
Leu Ser Cys Leu Leu Leu Thr Gly Ser Ser Ser Gly Ser Lys Leu Lys
 15                  20                  25                  30 gat cct gaa ctg agt tta aaa ggc acc cag cac atc atg caa gca ggc    387
Asp Pro Glu Leu Ser Leu Lys Gly Thr Gln His Ile Met Gln Ala Gly
                 35                  40                  45 cag aca ctg cat ctc caa tgc agg ggg gaa gca gcc cat aaa tgg tct    435
Gln Thr Leu His Leu Gln Cys Arg Gly Glu Ala Ala His Lys Trp Ser
             50                  55                  60 ttg cct gaa atg gtg agt aag gaa agc gaa agg ctg agc ata act aaa    483
Leu Pro Glu Met Val Ser Lys Glu Ser Glu Arg Leu Ser Ile Thr Lys
 65                  70                  75 tct gcc tgt gga aga aat ggc aaa caa ttc tgc agt act tta acc ttg    531
Ser Ala Cys Gly Arg Asn Gly Lys Gln Phe Cys Ser Thr Leu Thr Leu
         80                  85                  90 aac aca gct caa gca aac cac act ggc ttc tac agc tgc aaa tat cta    579
Asn Thr Ala Gln Ala Asn His Thr Gly Phe Tyr Ser Cys Lys Tyr Leu
 95                 100                 105                 110 gct gta cct act tca aag aag aag gaa aca gaa tct gca atc tat ata    627
Ala Val Pro Thr Ser Lys Lys Lys Glu Thr Glu Ser Ala Ile Tyr Ile
            115                 120                 125
```

```
ttt att agt gat aca ggt aga cct ttc gta gag atg tac agt gaa atc      675
Phe Ile Ser Asp Thr Gly Arg Pro Phe Val Glu Met Tyr Ser Glu Ile
            130                 135                 140 ccc gaa att ata cac atg act gaa gga agg gag ctc gtc att ccc tgc      723
Pro Glu Ile Ile His Met Thr Glu Gly Arg Glu Leu Val Ile Pro Cys
        145                 150                 155 cgg gtt acg tca cct aac atc act gtt act tta aaa aag ttt cca ctt      771
Arg Val Thr Ser Pro Asn Ile Thr Val Thr Leu Lys Lys Phe Pro Leu
    160                 165                 170 gac act ttg atc cct gat gga aaa cgc ata atc tgg gac agt aga aag      819
Asp Thr Leu Ile Pro Asp Gly Lys Arg Ile Ile Trp Asp Ser Arg Lys
175                 180                 185                 190 ggc ttc atc ata tca aat gca acg tac aaa gaa ata ggg ctt ctg acc      867
Gly Phe Ile Ile Ser Asn Ala Thr Tyr Lys Glu Ile Gly Leu Leu Thr
                195                 200                 205 tgt gaa gca aca gtc aat ggg cat ttg tat aag aca aac tat ctc aca      915
Cys Glu Ala Thr Val Asn Gly His Leu Tyr Lys Thr Asn Tyr Leu Thr
            210                 215                 220 cat cga caa acc aat aca atc ata gat gtc caa ata agc aca cca cgc      963
His Arg Gln Thr Asn Thr Ile Ile Asp Val Gln Ile Ser Thr Pro Arg
        225                 230                 235 cca gtc aaa tta ctt aga ggc cat act ctt gtc ctc aat tgt act gct     1011
Pro Val Lys Leu Leu Arg Gly His Thr Leu Val Leu Asn Cys Thr Ala
    240                 245                 250 acc act ccc ttg aac acg aga gtt caa atg acc tgg agt tac cct gat     1059
Thr Thr Pro Leu Asn Thr Arg Val Gln Met Thr Trp Ser Tyr Pro Asp
255                 260                 265                 270 gaa aaa aat aag aga gct tcc gta agg cga cga att gac caa agc aat     1107
Glu Lys Asn Lys Arg Ala Ser Val Arg Arg Arg Ile Asp Gln Ser Asn
                275                 280                 285 tcc cat gcc aac ata ttc tac agt gtt ctt act att gac aaa atg cag     1155
Ser His Ala Asn Ile Phe Tyr Ser Val Leu Thr Ile Asp Lys Met Gln
            290                 295                 300 aac aaa gac aaa gga ctt tat act tgt cgt gta agg agt gga cca tca     1203
Asn Lys Asp Lys Gly Leu Tyr Thr Cys Arg Val Arg Ser Gly Pro Ser
        305                 310                 315 ttc aaa tct gtt aac acc tca gtg cat ata tat gat aaa gca ttc atc     1251
Phe Lys Ser Val Asn Thr Ser Val His Ile Tyr Asp Lys Ala Phe Ile
    320                 325                 330 act gtg aaa cat cga aaa cag cag gtg ctt gaa acc gta gct ggc aag     1299
Thr Val Lys His Arg Lys Gln Gln Val Leu Glu Thr Val Ala Gly Lys
335                 340                 345                 350 cgg tct tac cgg ctc tct atg aaa gtg aag gca ttt ccc tcg ccg gaa     1347
Arg Ser Tyr Arg Leu Ser Met Lys Val Lys Ala Phe Pro Ser Pro Glu
                355                 360                 365 gtt gta tgg tta aaa gat ggg tta cct gcg act gag aaa tct gct cgc     1395
Val Val Trp Leu Lys Asp Gly Leu Pro Ala Thr Glu Lys Ser Ala Arg
            370                 375                 380 tat ttg act cgt ggc tac tcg tta att atc aag gac gta act gaa gag     1443
Tyr Leu Thr Arg Gly Tyr Ser Leu Ile Ile Lys Asp Val Thr Glu Glu
        385                 390                 395 gat gca ggg aat tat aca atc ttg ctg agc ata aaa cag tca aat gtg     1491
Asp Ala Gly Asn Tyr Thr Ile Leu Leu Ser Ile Lys Gln Ser Asn Val
    400                 405                 410 ttt aaa aac ctc act gcc act cta att gtc aat gtg aaa ccc cag att     1539
Phe Lys Asn Leu Thr Ala Thr Leu Ile Val Asn Val Lys Pro Gln Ile
415                 420                 425                 430 tac gaa aag gcc gtg tca tcg ttt cca gac ccg gct ctc tac cca ctg     1587
Tyr Glu Lys Ala Val Ser Ser Phe Pro Asp Pro Ala Leu Tyr Pro Leu
```

-continued

|     |     | 435 |     |     |     | 440 |     |     |     | 445 |     |     |     |      |
|-----|-----|-----|-----|-----|-----|-----|-----|-----|-----|-----|-----|-----|-----|------|
| ggc | agc | aga | caa | atc | ctg | act | tgt | acc | gca | tat | ggt | atc | cct | caa | cct | 1635 |
| Gly | Ser | Arg | Gln | Ile | Leu | Thr | Cys | Thr | Ala | Tyr | Gly | Ile | Pro | Gln | Pro |      |
|     |     |     | 450 |     |     |     | 455 |     |     |     | 460 |     |     |     |     |      | aca atc aag tgg ttc tgg cac ccc tgt aac cat aat cat tcc gaa gca  1683
Thr Ile Lys Trp Phe Trp His Pro Cys Asn His Asn His Ser Glu Ala
        465                 470                 475 agg tgt gac ttt tgt tcc aat aat gaa gag tcc ttt atc ctg gat gct  1731
Arg Cys Asp Phe Cys Ser Asn Asn Glu Glu Ser Phe Ile Leu Asp Ala
        480                 485                 490 gac agc aac atg gga aac aga att gag agc atc act cag cgc atg gca  1779
Asp Ser Asn Met Gly Asn Arg Ile Glu Ser Ile Thr Gln Arg Met Ala
495                 500                 505                 510 ata ata gaa gga aag aat aag atg gct agc acc ttg gtt gtg gct gac  1827
Ile Ile Glu Gly Lys Asn Lys Met Ala Ser Thr Leu Val Val Ala Asp
                515                 520                 525 tct aga att tct gga atc tac att tgc ata gct tcc aat aaa gtt ggg  1875
Ser Arg Ile Ser Gly Ile Tyr Ile Cys Ile Ala Ser Asn Lys Val Gly
                530                 535                 540 act gtg gga aga aac ata agc ttt tat atc aca gat gtg cca aat ggg  1923
Thr Val Gly Arg Asn Ile Ser Phe Tyr Ile Thr Asp Val Pro Asn Gly
        545                 550                 555 ttt cat gtt aac ttg gaa aaa atg ccg acg gaa gga gag gac ctg aaa  1971
Phe His Val Asn Leu Glu Lys Met Pro Thr Glu Gly Glu Asp Leu Lys
        560                 565                 570 ctg tct tgc aca gtt aac aag ttc tta tac aga gac gtt act tgg att  2019
Leu Ser Cys Thr Val Asn Lys Phe Leu Tyr Arg Asp Val Thr Trp Ile
575                 580                 585                 590 tta ctg cgg aca gtt aat aac aga aca atg cac tac agt att agc aag  2067
Leu Leu Arg Thr Val Asn Asn Arg Thr Met His Tyr Ser Ile Ser Lys
                595                 600                 605 caa aaa atg gcc atc act aag gag cac tcc atc act ctt aat ctt acc  2115
Gln Lys Met Ala Ile Thr Lys Glu His Ser Ile Thr Leu Asn Leu Thr
                610                 615                 620 atc atg aat gtt tcc ctg caa gat tca ggc acc tat gcc tgc aga gcc  2163
Ile Met Asn Val Ser Leu Gln Asp Ser Gly Thr Tyr Ala Cys Arg Ala
625                 630                 635 agg aat gta tac aca ggg gaa gaa atc ctc cag aag aaa gaa att aca  2211
Arg Asn Val Tyr Thr Gly Glu Glu Ile Leu Gln Lys Lys Glu Ile Thr
        640                 645                 650 atc aga gat cag gaa gca cca tac ctc ctg cga aac ctc agt gat cac  2259
Ile Arg Asp Gln Glu Ala Pro Tyr Leu Leu Arg Asn Leu Ser Asp His
655                 660                 665                 670 aca gtg gcc atc agc agt tcc acc act tta gac tgt cat gct aat ggt  2307
Thr Val Ala Ile Ser Ser Ser Thr Thr Leu Asp Cys His Ala Asn Gly
                675                 680                 685 gtc ccc gag cct cag atc act tgg ttt aaa aac aac cac aaa ata caa  2355
Val Pro Glu Pro Gln Ile Thr Trp Phe Lys Asn Asn His Lys Ile Gln
                690                 695                 700 caa gag cct gga att att tta gga cca gga agc agc acg ctg ttt att  2403
Gln Glu Pro Gly Ile Ile Leu Gly Pro Gly Ser Ser Thr Leu Phe Ile
        705                 710                 715 gaa aga gtc aca gaa gag gat gaa ggt gtc tat cac tgc aaa gcc acc  2451
Glu Arg Val Thr Glu Glu Asp Glu Gly Val Tyr His Cys Lys Ala Thr
        720                 725                 730 aac cag aag ggc tct gtg gaa agt tca gca tac ctc act gtt caa gga  2499
Asn Gln Lys Gly Ser Val Glu Ser Ser Ala Tyr Leu Thr Val Gln Gly
735                 740                 745                 750 acc tcg gac aag tct aat ctg gag ctg atc act cta aca tgc acc tgt  2547

```
Thr Ser Asp Lys Ser Asn Leu Glu Leu Ile Thr Leu Thr Cys Thr Cys
            755                 760                 765 gtg gct gcg act ctc ttc tgg ctc cta tta acc ctc ctt atc cga aaa      2595
Val Ala Ala Thr Leu Phe Trp Leu Leu Leu Thr Leu Leu Ile Arg Lys
        770                 775                 780 atg aaa agg tct tct tct gaa ata aag act gac tac cta tca att ata      2643
Met Lys Arg Ser Ser Ser Glu Ile Lys Thr Asp Tyr Leu Ser Ile Ile
            785                 790                 795 atg gac cca gat gaa gtt cct ttg gat gag cag tgt gag cgg ctc cct      2691
Met Asp Pro Asp Glu Val Pro Leu Asp Glu Gln Cys Glu Arg Leu Pro
        800                 805                 810 tat gat gcc agc aag tgg gag ttt gcc cgg gag aga ctt aaa ctg ggc      2739
Tyr Asp Ala Ser Lys Trp Glu Phe Ala Arg Glu Arg Leu Lys Leu Gly
815                 820                 825                 830 aaa tca ctt gga aga ggg gct ttt gga aaa gtg gtt caa gca tca gca      2787
Lys Ser Leu Gly Arg Gly Ala Phe Gly Lys Val Val Gln Ala Ser Ala
                835                 840                 845 ttt ggc att aag aaa tca cct acg tgc cgg act gtg gct gtg aaa atg      2835
Phe Gly Ile Lys Lys Ser Pro Thr Cys Arg Thr Val Ala Val Lys Met
            850                 855                 860 ctg aaa gag ggg gcc acg gcc agc gag tac aaa gct ctg atg act gag      2883
Leu Lys Glu Gly Ala Thr Ala Ser Glu Tyr Lys Ala Leu Met Thr Glu
        865                 870                 875 cta aaa atc ttg acc cac att ggc cac cat ctg aac gtg gtt aac ctg      2931
Leu Lys Ile Leu Thr His Ile Gly His His Leu Asn Val Val Asn Leu
880                 885                 890 ctg gga gcc tgc acc aag caa gga ggg cct ctg atg gtg att gtt gaa      2979
Leu Gly Ala Cys Thr Lys Gln Gly Gly Pro Leu Met Val Ile Val Glu
895                 900                 905                 910 tac tgc aaa tat gga aat ctc tcc aac tac ctc aag agc aaa cgt gac      3027
Tyr Cys Lys Tyr Gly Asn Leu Ser Asn Tyr Leu Lys Ser Lys Arg Asp
                915                 920                 925 tta ttt ttt ctc aac aag gat gca gca cta cac atg gag cct aag aaa      3075
Leu Phe Phe Leu Asn Lys Asp Ala Ala Leu His Met Glu Pro Lys Lys
            930                 935                 940 gaa aaa atg gag cca ggc ctg gaa caa ggc aag aaa cca aga cta gat      3123
Glu Lys Met Glu Pro Gly Leu Glu Gln Gly Lys Lys Pro Arg Leu Asp
        945                 950                 955 agc gtc acc agc agc gaa agc ttt gcg agc tcc ggc ttt cag gaa gat      3171
Ser Val Thr Ser Ser Glu Ser Phe Ala Ser Ser Gly Phe Gln Glu Asp
        960                 965                 970 aaa agt ctg agt gat gtt gag gaa gag gag gat tct gac ggt ttc tac      3219
Lys Ser Leu Ser Asp Val Glu Glu Glu Glu Asp Ser Asp Gly Phe Tyr
975                 980                 985                 990 aag gag ccc atc act atg gaa gat ctg att tct tac agt ttt caa gtg      3267
Lys Glu Pro Ile Thr Met Glu Asp Leu Ile Ser Tyr Ser Phe Gln Val
                995                 1000                1005 gcc aga ggc atg gag ttc ctg tct tcc aga aag tgc att cat cgg gac      3315
Ala Arg Gly Met Glu Phe Leu Ser Ser Arg Lys Cys Ile His Arg Asp
            1010                1015                1020 ctg gca gcg aga aac att ctt tta tct gag aac aac gtg gtg aag att      3363
Leu Ala Ala Arg Asn Ile Leu Leu Ser Glu Asn Asn Val Val Lys Ile
        1025                1030                1035 tgt gat ttt ggc ctt gcc cgg gat att tat aag aac ccc gat tat gtg      3411
Cys Asp Phe Gly Leu Ala Arg Asp Ile Tyr Lys Asn Pro Asp Tyr Val
        1040                1045                1050 aga aaa gga gat act cga ctt cct ctg aaa tgg atg gct ccc gaa tct      3459
Arg Lys Gly Asp Thr Arg Leu Pro Leu Lys Trp Met Ala Pro Glu Ser
1055                1060                1065                1070
```

| | |
|---|---|
| atc ttt gac aaa atc tac agc acc aag agc gac gtg tgg tct tac gga<br>Ile Phe Asp Lys Ile Tyr Ser Thr Lys Ser Asp Val Trp Ser Tyr Gly<br>1075                        1080                   1085 | 3507 |
| gta ttg ctg tgg gaa atc ttc tcc tta ggt ggg tct cca tac cca gga<br>Val Leu Leu Trp Glu Ile Phe Ser Leu Gly Gly Ser Pro Tyr Pro Gly<br>               1090                   1095                 1100 | 3555 |
| gta caa atg gat gag gac ttt tgc agt cgc ctg agg gaa ggc atg agg<br>Val Gln Met Asp Glu Asp Phe Cys Ser Arg Leu Arg Glu Gly Met Arg<br>1105                        1110                   1115 | 3603 |
| atg aga gct cct gag tac tct act cct gaa atc tat cag atc atg ctg<br>Met Arg Ala Pro Glu Tyr Ser Thr Pro Glu Ile Tyr Gln Ile Met Leu<br>               1120                   1125                 1130 | 3651 |
| gac tgc tgg cac aga gac cca aaa gaa agg cca aga ttt gca gaa ctt<br>Asp Cys Trp His Arg Asp Pro Lys Glu Arg Pro Arg Phe Ala Glu Leu<br>1135                        1140                   1145                 1150 | 3699 |
| gtg gaa aaa cta ggt gat ttg ctt caa gca aat gta caa cag gat ggt<br>Val Glu Lys Leu Gly Asp Leu Leu Gln Ala Asn Val Gln Gln Asp Gly<br>               1155                   1160                 1165 | 3747 |
| aaa gac tac atc cca atc aat gcc ata ctg aca gga aat agt ggg ttt<br>Lys Asp Tyr Ile Pro Ile Asn Ala Ile Leu Thr Gly Asn Ser Gly Phe<br>1170                        1175                   1180 | 3795 |
| aca tac tca act cct gcc ttc tct gag gac ttc ttc aag gaa agt att<br>Thr Tyr Ser Thr Pro Ala Phe Ser Glu Asp Phe Phe Lys Glu Ser Ile<br>               1185                   1190                 1195 | 3843 |
| tca gct ccg aag ttt aat tca gga agc tct gat gat gtc aga tat gta<br>Ser Ala Pro Lys Phe Asn Ser Gly Ser Ser Asp Asp Val Arg Tyr Val<br>1200                        1205                   1210 | 3891 |
| aat gct ttc aag ttc atg agc ctg gaa aga atc aaa acc ttt gaa gaa<br>Asn Ala Phe Lys Phe Met Ser Leu Glu Arg Ile Lys Thr Phe Glu Glu<br>1215                        1220                   1225                 1230 | 3939 |
| ctt tta ccg aat gcc acc tcc atg ttt gat gac tac cag ggc gac agc<br>Leu Leu Pro Asn Ala Thr Ser Met Phe Asp Asp Tyr Gln Gly Asp Ser<br>               1235                   1240                 1245 | 3987 |
| agc act ctg ttg gcc tct ccc atg ctg aag cgc ttc acc tgg act gac<br>Ser Thr Leu Leu Ala Ser Pro Met Leu Lys Arg Phe Thr Trp Thr Asp<br>1250                        1255                   1260 | 4035 |
| agc aaa ccc aag gcc tcg ctc aag att gac ttg aga gta acc agt aaa<br>Ser Lys Pro Lys Ala Ser Leu Lys Ile Asp Leu Arg Val Thr Ser Lys<br>               1265                   1270                 1275 | 4083 |
| agt aag gag tcg ggg ctg tct gat gtc agc agg ccc agt ttc tgc cat<br>Ser Lys Glu Ser Gly Leu Ser Asp Val Ser Arg Pro Ser Phe Cys His<br>1280                        1285                   1290 | 4131 |
| tcc agc tgt ggg cac gtc agc gaa ggc aag cgc agg ttc acc tac gac<br>Ser Ser Cys Gly His Val Ser Glu Gly Lys Arg Arg Phe Thr Tyr Asp<br>1295                        1300                   1305                 1310 | 4179 |
| cac gct gag ctg gaa agg aaa atc gcg tgc tgc tcc ccg ccc cca gac<br>His Ala Glu Leu Glu Arg Lys Ile Ala Cys Cys Ser Pro Pro Pro Asp<br>               1315                   1320                 1325 | 4227 |
| tac aac tcg gtg gtc ctg tac tcc acc cca ccc atc tag agtttgacac<br>Tyr Asn Ser Val Val Leu Tyr Ser Thr Pro Pro Ile<br>               1330                   1335 | 4276 |
| gaagccttat ttctagaagc acatgtgtat ttatacccc aggaaactag cttttgccag | 4336 |
| tattatgcat atataagttt acaccttat ctttccatgg gagccagctg cttttttgtga | 4396 |
| ttttttaat agtgcttttt tttttgact aacaagaatg taactccaga tagagaaata | 4456 |
| gtgacaagtg aagaacacta ctgctaaatc ctcatgttac tcagtgttag agaaatcctt | 4516 |
| cctaaaccca atgacttccc tgctccaacc ccgccacct cagggcacgc aggaccagtt | 4576 |
| tgattgagga gctgcactga tcacccaatg catcacgtac cccactgggc cagccctgca | 4636 |

-continued

```
gcccaaaacc cagggcaaca agcccgttag ccccagggga tcactggctg gcctgagcaa      4696
catctcggga gtcctctagc aggcctaaga catgtgagga ggaaaaggaa aaaaagcaaa      4756
aagcaaggga gaaaagagaa accgggagaa ggcatgagaa agaatttgag acgcaccatg      4816
tgggcacgga gggggacggg gctcagcaat gccatttcag tggcttccca gctctgaccc      4876
ttctacattt gagggcccag ccaggagcag atggacagcg atgaggggac attttctgga      4936 ttctggagg caagaaaagg acaaatatct tttttggaac taaagcaaat tttagacctt       4996
tacctatgga agtggttcta tgtccattct cattcgtggc atgttttgat ttgtagcact      5056
gagggtggca ctcaactctg agcccatact tttggctcct ctagtaagat gcactgaaaa      5116
cttagccaga gttaggttgt ctccaggcca tgatggcctt acactgaaaa tgtcacattc      5176
tattttgggt attaatatat agtccagaca cttaactcaa tttcttggta ttattctgtt      5236
ttgcacagtt agttgtgaaa gaaagctgag aagaatgaaa atgcagtcct gaggagagtt      5296
ttctccatat caaacgagg gctgatggag gaaaaggtc aataaggtca agggaagacc        5356
ccgtctctat accaaccaaa ccaattcacc aacacagttg ggacccaaaa cacaggaagt      5416
cagtcacgtt tccttttcat ttaatgggga ttccactatc tcacactaat ctgaaaggat      5476
gtggaagagc attagctggc gcatattaag cactttaagc tccttgagta aaaaggtggt      5536
atgtaattta tgcaaggtat ttctccagtt gggactcagg atattagtta atgagccatc      5596
actagaagaa aagcccattt tcaactgctt tgaaacttgc ctgggtctg agcatgatgg       5656 gaatagggag acagggtagg aaagggcgcc tactcttcag ggtctaaaga tcaagtgggc      5716
cttggatcgc taagctggct ctgtttgatg ctatttatgc aagttagggt ctatgtattt      5776
aggatgcgcc tactcttcag ggtctaaaga tcaagtgggc cttggatcgc taagctggct      5836
ctgtttgatg ctatttatgc aagttagggt ctatgtattt aggatgtctg caccttctgc      5896
agccagtcag aagctggaga ggcaacagtg gattgctgct tcttggggag aagagtatgc      5956
ttccttttat ccatgtaatt taactgtaga acctgagctc taagtaaccg aagaatgtat      6016
gcctctgttc ttatgtgcca catccttgtt taaaggctct ctgtatgaag agatgggacc      6076
gtcatcagca cattccctag tgagcctact ggctcctggc agcggctttt gtggaagact      6136
cactagccag aagagaggag tgggacagtc ctctccacca agatctaaat ccaaacaaaa      6196
gcaggctaga gccagaagag aggacaaatc tttgttgttc ctcttcttta cacatacgca      6256
aaccacctgt gacagctggc aatttataaa atcaggtaac tggaaggagg ttaaactcag      6316
aaaaaagaag acctcagtca attctctact tttttttttt tttttccaaa tcagataata      6376
gcccagcaaa tagtgataac aaataaaacc ttagctgttc atgtcttgat ttcaataatt      6436
aattcttaat cattaagaga ccataataaa tactccttt caagagaaaa gcaaaaccat       6496
tagaattgtt actcagctcc ttcaaactca ggtttgtagc atacatgagt ccatccatca      6556
gtcaaagaat ggttccatct ggagtcttaa tgtagaaaga aaatggaga cttgtaataa       6616 tgagctagtt acaaagtgct tgttcattaa aatagcactg aaaattgaaa catgaattaa      6676
ctgataatat tccaatcatt tgccatttat gacaaaaatg gttggcacta acaaagaacg      6736
agcacttcct ttcagagttt ctgagataat gtacgtggaa cagtctgggt ggaatggggc      6796
tgaaaccatg tgcaagtctg tgtcttgtca gtccaagaag tgacaccgag atgttaattt      6856
tagggacccg tgccttgttt cctagcccac aagaatgcaa acatcaaaca gatactcgct      6916
agcctcattt aaattgatta aggaggagt gcatctttgg ccgacagtgg tgtaactgtg        6976
```

-continued

```
tgtgtgtgtg tgtgtgtgtg tgtgtgtgtg tgtgtgtggg tgtgggtgta tgtgtgtttt      7036
gtgcataact atttaaggaa actggaattt taaagttact tttatacaaa ccaagaatat      7096
atgctacaga tataagacag acatggtttg gtcctatatt tctagtcatg atgaatgtat      7156
tttgtatacc atcttcatat aatatactta aaaatatttc ttaattggga tttgtaatcg      7216
taccaactta attgataaac ttggcaactg cttttatgtt ctgtctcctt ccataaattt      7276
ttcaaaatac taattcaaca agaaaaagc tcttttttt cctaaaataa actcaaattt       7336
atccttgttt agagcagaga aaattaaga aaactttga aatggtctca aaaaattgct        7396 aaatatttc aatggaaaac taaatgttag tttagctgat tgtatggggt tttcgaacct       7456
ttcacttttt gtttgttta cctatttcac aactgtgtaa attgccaata attcctgtcc      7516
atgaaaatgc aaattatcca gtgtagatat atttgaccat cacccctatgg atattggcta   7576 gttttgcctt tattaagcaa attcatttca gcctgaatgt ctgcctatat attctctgct    7636
ctttgtattc tcctttgaac ccgttaaaac atcctgtggc actc                      7680
```

```
<210> SEQ ID NO 4
<211> LENGTH: 18
<212> TYPE: DNA
<213> ORGANISM: Artificial Sequence
<220> FEATURE:
<223> OTHER INFORMATION: PCR Primer

<400> SEQUENCE: 4
ccctcgccgg aagttgta                                                    18

<210> SEQ ID NO 5
<211> LENGTH: 26
<212> TYPE: DNA
<213> ORGANISM: Artificial Sequence
<220> FEATURE:
<223> OTHER INFORMATION: PCR Primer

<400> SEQUENCE: 5
ataattaacg agtagccacg agtcaa                                           26

<210> SEQ ID NO 6
<211> LENGTH: 26
<212> TYPE: DNA
<213> ORGANISM: Artificial Sequence
<220> FEATURE:
<223> OTHER INFORMATION: PCR Probe

<400> SEQUENCE: 6
acctgcgact gagaaatctg ctcgct                                           26

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                   19

<210> SEQ ID NO 8
<211> LENGTH: 20
<212> TYPE: DNA
<213> ORGANISM: Artificial Sequence
<220> FEATURE:
<223> OTHER INFORMATION: PCR Primer
```

-continued

```
<400> SEQUENCE: 8
gaagatggtg atgggatttc                                                      20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                      20

<210> SEQ ID NO 10
<211> LENGTH: 6055
<212> TYPE: DNA
<213> ORGANISM: Mus musculus
<220> FEATURE:
<221> NAME/KEY: CDS
<222> LOCATION: (27)...(4028)

<400> SEQUENCE: 10
ggccaacagg ccgcgtcttg ctcacc atg gtc agc tgc tgg gac acc gcg gtc         53
                              Met Val Ser Cys Trp Asp Thr Ala Val
                                1               5 ttg cct tac gcg ctg ctc ggg tgt ctg ctt ctc aca gga tat ggc tca         101
Leu Pro Tyr Ala Leu Leu Gly Cys Leu Leu Leu Thr Gly Tyr Gly Ser
 10              15                  20                  25 ggg tcg aag tta aaa gtg cct gaa ctg agt tta aaa ggc acc cag cat         149
Gly Ser Lys Leu Lys Val Pro Glu Leu Ser Leu Lys Gly Thr Gln His
             30                  35                  40 gtc atg caa gca ggc cag act ctc ttt ctc aag tgc aga ggg gag gca         197
Val Met Gln Ala Gly Gln Thr Leu Phe Leu Lys Cys Arg Gly Glu Ala
         45                  50                  55 gcc cac tca tgg tct ctg ccc acg acc gtg agc cag gag gac aaa agg         245
Ala His Ser Trp Ser Leu Pro Thr Thr Val Ser Gln Glu Asp Lys Arg
     60                  65                  70 ctg agc atc act ccc cca tcg gcc tgt ggg agg gat aac agg caa ttc         293
Leu Ser Ile Thr Pro Pro Ser Ala Cys Gly Arg Asp Asn Arg Gln Phe
 75                  80                  85 tgc agc acc ttg acc ttg gac acg gcg cag gcc aac cac acg ggc ctc         341
Cys Ser Thr Leu Thr Leu Asp Thr Ala Gln Ala Asn His Thr Gly Leu
 90                  95                 100                 105 tac acc tgt aga tac ctc cct aca tct act tcg aag aaa aag aaa gcg         389
Tyr Thr Cys Arg Tyr Leu Pro Thr Ser Thr Ser Lys Lys Lys Lys Ala
            110                 115                 120 gaa tct tca atc tac ata ttt gtt agt gat gca ggg agt cct ttc ata         437
Glu Ser Ser Ile Tyr Ile Phe Val Ser Asp Ala Gly Ser Pro Phe Ile
        125                 130                 135 gag atg cac act gac ata ccc aaa ctt gtg cac atg acg gaa gga aga         485
Glu Met His Thr Asp Ile Pro Lys Leu Val His Met Thr Glu Gly Arg
    140                 145                 150 cag ctc atc atc ccc tgc cgg gtg acg tca ccc aac gtc aca gtc acc         533
Gln Leu Ile Ile Pro Cys Arg Val Thr Ser Pro Asn Val Thr Val Thr
155                 160                 165 cta aaa aag ttt cca ttt gat act ctt acc cct gat ggg caa aga ata         581
Leu Lys Lys Phe Pro Phe Asp Thr Leu Thr Pro Asp Gly Gln Arg Ile
170                 175                 180                 185 aca tgg gac agt agg aga ggc ttt ata ata gca aat gca acg tac aaa         629
Thr Trp Asp Ser Arg Arg Gly Phe Ile Ile Ala Asn Ala Thr Tyr Lys
                190                 195                 200
```

```
gag ata gga ctg ctg aac tgc gaa gcc acc gtc aac ggg cac ctg tac      677
Glu Ile Gly Leu Leu Asn Cys Glu Ala Thr Val Asn Gly His Leu Tyr
            205                 210                 215 cag aca aac tat ctg acc cat cgg cag acc aat aca atc cta gat gtc      725
Gln Thr Asn Tyr Leu Thr His Arg Gln Thr Asn Thr Ile Leu Asp Val
        220                 225                 230 caa ata cgc ccg ccg agc cca gtg aga ctg ctc cac ggg cag act ctt      773
Gln Ile Arg Pro Pro Ser Pro Val Arg Leu Leu His Gly Gln Thr Leu
    235                 240                 245 gtc ctc aac tgc acc gcc acc acg gag ctc aat acg agg gtg caa atg      821
Val Leu Asn Cys Thr Ala Thr Thr Glu Leu Asn Thr Arg Val Gln Met
250                 255                 260                 265 agc tgg aat tac cct ggt aaa gca act aag aga gca tct ata agg cag      869
Ser Trp Asn Tyr Pro Gly Lys Ala Thr Lys Arg Ala Ser Ile Arg Gln
                270                 275                 280 cgg att gac cgg agc cat tcc cac aac aat gtg ttc cac agt gtt ctt      917
Arg Ile Asp Arg Ser His Ser His Asn Asn Val Phe His Ser Val Leu
            285                 290                 295 aag atc aac aat gtg gag agc cga gac aag ggg ctc tac acc tgt cgc      965
Lys Ile Asn Asn Val Glu Ser Arg Asp Lys Gly Leu Tyr Thr Cys Arg
        300                 305                 310 gtg aag agt ggg tcc tcg ttc cag tct ttc aac acc tcc gtg cat gtg     1013
Val Lys Ser Gly Ser Ser Phe Gln Ser Phe Asn Thr Ser Val His Val
    315                 320                 325 tat gaa aaa gga ttc atc agt gtg aaa cat cgg aag cag ccg gtg cag     1061
Tyr Glu Lys Gly Phe Ile Ser Val Lys His Arg Lys Gln Pro Val Gln
330                 335                 340                 345 gaa acc aca gca gga aga cgg tcc tat cgg ctg tcc atg aaa gtg aag     1109
Glu Thr Thr Ala Gly Arg Arg Ser Tyr Arg Leu Ser Met Lys Val Lys
                350                 355                 360 gcc ttc ccc tcc cca gaa atc gta tgg tta aaa gat ggc tcg cct gca     1157
Ala Phe Pro Ser Pro Glu Ile Val Trp Leu Lys Asp Gly Ser Pro Ala
            365                 370                 375 aca ttg aag tct gct cgc tat ttg gta cat ggc tac tca tta att atc     1205
Thr Leu Lys Ser Ala Arg Tyr Leu Val His Gly Tyr Ser Leu Ile Ile
        380                 385                 390 aaa gat gtg aca acc gag gat gca ggg gac tat acg atc ttg ctg ggc     1253
Lys Asp Val Thr Thr Glu Asp Ala Gly Asp Tyr Thr Ile Leu Leu Gly
    395                 400                 405 ata aag cag tca agg cta ttt aaa aac ctc act gcc act ctc att gta     1301
Ile Lys Gln Ser Arg Leu Phe Lys Asn Leu Thr Ala Thr Leu Ile Val
410                 415                 420                 425 aac gtg aaa cct cag atc tac gaa aag tcc gtg tcc tcg ctt cca agc     1349
Asn Val Lys Pro Gln Ile Tyr Glu Lys Ser Val Ser Ser Leu Pro Ser
                430                 435                 440 cca cct ctc tat ccg ctg ggc agc aga caa gtc ctc act tgc acc gtg     1397
Pro Pro Leu Tyr Pro Leu Gly Ser Arg Gln Val Leu Thr Cys Thr Val
            445                 450                 455 tat ggc atc cct cgg cca aca atc acg tgg ctc tgg cac ccc tgt cac     1445
Tyr Gly Ile Pro Arg Pro Thr Ile Thr Trp Leu Trp His Pro Cys His
        460                 465                 470 cac aat cac tcc aaa gaa agg tat gac ttc tgc act gag aat gaa gaa     1493
His Asn His Ser Lys Glu Arg Tyr Asp Phe Cys Thr Glu Asn Glu Glu
    475                 480                 485 tcc ttt atc ctg gat ccc agc agc aac tta gga aac aga att gag agc     1541
Ser Phe Ile Leu Asp Pro Ser Ser Asn Leu Gly Asn Arg Ile Glu Ser
490                 495                 500                 505 atc tct cag cgc atg acg gtc ata gaa gga aca aat aag acg gtt agc     1589
Ile Ser Gln Arg Met Thr Val Ile Glu Gly Thr Asn Lys Thr Val Ser
```

-continued

| | | | |
|---|---|---|---|
| aca ttg gtg gtg gct gac tct cag acc cct gga atc tac agc tgc cgg<br>Thr Leu Val Val Ala Asp Ser Gln Thr Pro Gly Ile Tyr Ser Cys Arg<br>525 530 535 | | | 1637 |
| gcc ttc aat aaa ata ggg act gtg gaa aga aac ata aaa ttt tat gtc<br>Ala Phe Asn Lys Ile Gly Thr Val Glu Arg Asn Ile Lys Phe Tyr Val<br>540 545 550 | | | 1685 |
| aca gat gtg ccg aat ggc ttt cac gtt tcc ttg gaa aag atg cca gcc<br>Thr Asp Val Pro Asn Gly Phe His Val Ser Leu Glu Lys Met Pro Ala<br>555 560 565 | | | 1733 |
| gaa gga gag gac ctg aaa ctg tcc tgt gtg gtc aat aaa ttc ctg tac<br>Glu Gly Glu Asp Leu Lys Leu Ser Cys Val Val Asn Lys Phe Leu Tyr<br>570 575 580 585 | | | 1781 |
| aga gac att acc tgg att ctg cta cgg aca gtt aac aac aga acc atg<br>Arg Asp Ile Thr Trp Ile Leu Leu Arg Thr Val Asn Asn Arg Thr Met<br>590 595 600 | | | 1829 |
| cac cat agt atc agc aag caa aaa atg gcc acc act caa gat tac tcc<br>His His Ser Ile Ser Lys Gln Lys Met Ala Thr Thr Gln Asp Tyr Ser<br>605 610 615 | | | 1877 |
| atc act ctg aac ctt gtc atc aag aac gtg tct cta gaa gac tcg ggc<br>Ile Thr Leu Asn Leu Val Ile Lys Asn Val Ser Leu Glu Asp Ser Gly<br>620 625 630 | | | 1925 |
| acc tat gcg tgc aga gcc agg aac ata tac aca ggg gaa gac atc ctt<br>Thr Tyr Ala Cys Arg Ala Arg Asn Ile Tyr Thr Gly Glu Asp Ile Leu<br>635 640 645 | | | 1973 |
| cgg aag aca gaa gtt ctc gtt aga gat tcg gaa gcg cca cac ctg ctt<br>Arg Lys Thr Glu Val Leu Val Arg Asp Ser Glu Ala Pro His Leu Leu<br>650 655 660 665 | | | 2021 |
| caa aac ctc agt gac tac gag gtc tcc atc agt ggc tct acg acc tta<br>Gln Asn Leu Ser Asp Tyr Glu Val Ser Ile Ser Gly Ser Thr Thr Leu<br>670 675 680 | | | 2069 |
| gac tgt caa gct aga ggt gtc ccc gcg cct cag atc act tgg ttc aaa<br>Asp Cys Gln Ala Arg Gly Val Pro Ala Pro Gln Ile Thr Trp Phe Lys<br>685 690 695 | | | 2117 |
| aac aac cac aaa ata caa caa gaa ccg gga att att tta gga cca gga<br>Asn Asn His Lys Ile Gln Gln Glu Pro Gly Ile Ile Leu Gly Pro Gly<br>700 705 710 | | | 2165 |
| aac agc acg ctg ttt att gaa aga gtc aca gag gag gat gag ggt gtc<br>Asn Ser Thr Leu Phe Ile Glu Arg Val Thr Glu Glu Asp Glu Gly Val<br>715 720 725 | | | 2213 |
| tat agg tgc cga gcc acc aac cag aag ggg gcc gtg gaa agc gca gcc<br>Tyr Arg Cys Arg Ala Thr Asn Gln Lys Gly Ala Val Glu Ser Ala Ala<br>730 735 740 745 | | | 2261 |
| tac ctc acc gtg caa gga acc tca gac aag tca aac ctg gag ctg atc<br>Tyr Leu Thr Val Gln Gly Thr Ser Asp Lys Ser Asn Leu Glu Leu Ile<br>750 755 760 | | | 2309 |
| acg ctc acg tgc aca tgc gtg gct gcg acc ctc ttt tgg ctc ctt cta<br>Thr Leu Thr Cys Thr Cys Val Ala Ala Thr Leu Phe Trp Leu Leu Leu<br>765 770 775 | | | 2357 |
| act ctc ttc atc aga aaa ctg aag cgg tct tct tcc gaa gta aag aca<br>Thr Leu Phe Ile Arg Lys Leu Lys Arg Ser Ser Ser Glu Val Lys Thr<br>780 785 790 | | | 2405 |
| gac tac ctg tca atc att atg gac cca gat gaa gtt ccc ctg gat gag<br>Asp Tyr Leu Ser Ile Ile Met Asp Pro Asp Glu Val Pro Leu Asp Glu<br>795 800 805 | | | 2453 |
| cag tgt gaa cgg ctg ccc tat gat gcc agc aag tgg gag ttt gca cgg<br>Gln Cys Glu Arg Leu Pro Tyr Asp Ala Ser Lys Trp Glu Phe Ala Arg<br>810 815 820 825 | | | 2501 |
| gag aga ctg aaa cta ggc aaa tcg ctc gga aga ggg gct ttt ggg aaa | | | 2549 |

```
Glu Arg Leu Lys Leu Gly Lys Ser Leu Gly Arg Gly Ala Phe Gly Lys
                830                 835                 840 gtc gtt caa gcc tct gca ttt ggc att aag aaa tca ccc acc tgc cgg    2597
Val Val Gln Ala Ser Ala Phe Gly Ile Lys Lys Ser Pro Thr Cys Arg
            845                 850                 855 act gtg gct gtg aag atg ttg aaa gag ggg gcc aca gcc agt gag tac    2645
Thr Val Ala Val Lys Met Leu Lys Glu Gly Ala Thr Ala Ser Glu Tyr
        860                 865                 870 aaa gct ctg atg acc gaa ctc aag atc ttg acc cac atc ggc cat cat    2693
Lys Ala Leu Met Thr Glu Leu Lys Ile Leu Thr His Ile Gly His His
    875                 880                 885 ctg aat gtg gtt aac ctc ctg gga gcc tgc acg aag caa gga ggg cct    2741
Leu Asn Val Val Asn Leu Leu Gly Ala Cys Thr Lys Gln Gly Gly Pro
890                 895                 900                 905 ctg atg gtg atc gtg gaa tac tgc aaa tac gga aac ctg tcc aac tac    2789
Leu Met Val Ile Val Glu Tyr Cys Lys Tyr Gly Asn Leu Ser Asn Tyr
                910                 915                 920 ctc aag agc aaa cgt gac tta ttc tgt ctc aac aag gac gca gcc ttg    2837
Leu Lys Ser Lys Arg Asp Leu Phe Cys Leu Asn Lys Asp Ala Ala Leu
            925                 930                 935 cat atg gag ctc aag aaa gag agc ctg gaa cca ggc ctg gag cag ggc    2885
His Met Glu Leu Lys Lys Glu Ser Leu Glu Pro Gly Leu Glu Gln Gly
        940                 945                 950 cag aag ccc cgc cta gac agt gtc agc agc tca agt gtc acc agc tcc    2933
Gln Lys Pro Arg Leu Asp Ser Val Ser Ser Ser Ser Val Thr Ser Ser
    955                 960                 965 agc ttc cct gaa gac cga agc gtg agc gat gtg gaa gga gac gag gat    2981
Ser Phe Pro Glu Asp Arg Ser Val Ser Asp Val Glu Gly Asp Glu Asp
970                 975                 980                 985 tac agt gag atc tcc aag cag ccc ctc acc atg gaa gac ctg att tcc    3029
Tyr Ser Glu Ile Ser Lys Gln Pro Leu Thr Met Glu Asp Leu Ile Ser
                990                 995                 1000 tac agt ttc caa gtg gcc aga ggc atg gag ttt ctg tcc tcc aga aag    3077
Tyr Ser Phe Gln Val Ala Arg Gly Met Glu Phe Leu Ser Ser Arg Lys
            1005                1010                1015 tgc att cat cgg gac ctg gca gcg aga aac atc ctt tta tct gag aac    3125
Cys Ile His Arg Asp Leu Ala Ala Arg Asn Ile Leu Leu Ser Glu Asn
        1020                1025                1030 aat gtg gtg aag att tgc gac ttt ggc ctg gcc cgg gat att tat aag    3173
Asn Val Val Lys Ile Cys Asp Phe Gly Leu Ala Arg Asp Ile Tyr Lys
    1035                1040                1045 aac cct gat tat gtg agg aga gga gat act cga ctt ccc cta aaa tgg    3221
Asn Pro Asp Tyr Val Arg Arg Gly Asp Thr Arg Leu Pro Leu Lys Trp
1050                1055                1060                1065 atg gct cct gaa tcc atc ttt gac aag gtc tac agc acc aag agc gat    3269
Met Ala Pro Glu Ser Ile Phe Asp Lys Val Tyr Ser Thr Lys Ser Asp
                1070                1075                1080 gtg tgg tcc tat ggc gtg ttg ctg tgg gag atc ttc tcc tta ggg ggt    3317
Val Trp Ser Tyr Gly Val Leu Leu Trp Glu Ile Phe Ser Leu Gly Gly
            1085                1090                1095 tct cca tac cca gga gtg caa atg gat gaa gac ttc tgc agc cgc ctg    3365
Ser Pro Tyr Pro Gly Val Gln Met Asp Glu Asp Phe Cys Ser Arg Leu
        1100                1105                1110 aag gaa ggc atg cgg atg aga acc ccg gag tat gcc aca cct gaa atc    3413
Lys Glu Gly Met Arg Met Arg Thr Pro Glu Tyr Ala Thr Pro Glu Ile
    1115                1120                1125 tac caa atc atg ttg gat tgc tgg cac aaa gac ccc aaa gag agg ccc    3461
Tyr Gln Ile Met Leu Asp Cys Trp His Lys Asp Pro Lys Glu Arg Pro
1130                1135                1140                1145
```

```
cgg ttt gct gaa ctt gtg gag aaa ctt ggt gac ctg ctt caa gcc aac      3509
Arg Phe Ala Glu Leu Val Glu Lys Leu Gly Asp Leu Leu Gln Ala Asn
        1150                1155                1160 gtc caa cag gat ggg aaa gat tac atc ccc ctc aat gcc ata ctg act      3557
Val Gln Gln Asp Gly Lys Asp Tyr Ile Pro Leu Asn Ala Ile Leu Thr
    1165                1170                1175 aga aac agt agc ttc aca tac tcg acc ccc acc ttc tct gag gac ctt      3605
Arg Asn Ser Ser Phe Thr Tyr Ser Thr Pro Thr Phe Ser Glu Asp Leu
        1180                1185                1190 ttc aag gac ggc ttt gca gat cca cat ttt cat tcc gga agc tct gat      3653
Phe Lys Asp Gly Phe Ala Asp Pro His Phe His Ser Gly Ser Ser Asp
    1195                1200                1205 gat gtg aga tat gta aac gct ttc aaa ttc atg agc ctg gaa aga atc      3701
Asp Val Arg Tyr Val Asn Ala Phe Lys Phe Met Ser Leu Glu Arg Ile
1210                1215                1220                1225 aaa acc ttt gag gag ctt tca ccg aac tcc acc tcc atg ttt gag gac      3749
Lys Thr Phe Glu Glu Leu Ser Pro Asn Ser Thr Ser Met Phe Glu Asp
        1230                1235                1240 tat cag ctg gac act agc act ctg ctg ggc tcc ccc ttg ctg aag cgg      3797
Tyr Gln Leu Asp Thr Ser Thr Leu Leu Gly Ser Pro Leu Leu Lys Arg
    1245                1250                1255 ttc acc tgg act gag acc aag ccc aag gcc tcc atg aag ata gac ttg      3845
Phe Thr Trp Thr Glu Thr Lys Pro Lys Ala Ser Met Lys Ile Asp Leu
        1260                1265                1270 aga ata gcg agt aaa agc aag gag gcg gga ctt tcc gat ctg ccg agg      3893
Arg Ile Ala Ser Lys Ser Lys Glu Ala Gly Leu Ser Asp Leu Pro Arg
    1275                1280                1285 ccc agc ttc tgc ttc tcc agc tgt ggc cac atc agg ccc gtg cag gac      3941
Pro Ser Phe Cys Phe Ser Ser Cys Gly His Ile Arg Pro Val Gln Asp
1290                1295                1300                1305 gat gaa tct gag ctg gga aag gag tcc tgc tgt tct cca ccc cca gac      3989
Asp Glu Ser Glu Leu Gly Lys Glu Ser Cys Cys Ser Pro Pro Pro Asp
        1310                1315                1320 tac aac tcc gtg gtg ttg tac tcc tcc ccg ccc gcc taa agcttctcac       4038
Tyr Asn Ser Val Val Leu Tyr Ser Ser Pro Pro Ala
    1325                1330 cagccccgac aaccagcccc tgacagtatt atacatctat gagtttacac ctattccgct    4098
ccacaggagc cagctgcttt tcgtgacctt taatcgtgct tttttgtttt ttgttttgtt    4158
tgttgttgct gttttgacta acaagaatgt aaccccagtt agtgacgtgt gaagaatact    4218
attgttagag aaatccccc cgcaaagcct cagggtaacc tggacaggaa ggagcaggtg     4278
cctctggcga ccgcccgccc accggccatg gccccaccca ccctccctgc agctgtggga    4338
ctagaggcag taagcccatt agctcatggc tgcatgcact gacctgctct gtctctctta    4398
tggaggaaag ggagaacaga gcaaacagga ggcacaggaa aaggctttgg gatgcgtccg    4458
tcctgtggag cccgtgcagg aggggctcc gctatgccac ttcagtgact tctcactcct     4518
ggcctccgct gtttcgggcc ccttccaag aggtatcaga gcagaacatg agggacgttt     4578
cctagaccag ggcacatgtt ctcgggaacc acagttaatc ttaaatcttt tcccgggagt    4638
cttctgttgt ctgtttacca tccaaagcat atttaacatg tgtcagtggg ggtggcgctt    4698
ggcttctgag gccagagcca tcatcagttc ctctagtgag atgcattgag gtcatacccca   4758 agcttgcagg cctgaccttc gcatactgct cacggggagt taagtggtcc agtttggcct    4818
agtaaggttg cctactgatg ggctcaaaag ccacatttta aacaggtttt atctcaagta    4878
ttaatatata gacaagacac ttatgcatta tcctgtttta tatatccaat gaatataact    4938
ggggcgagtt aagagtcatg gtctagaaaa ggggtttctc tgtacccaaa tcgggctggt    4998
```

-continued

```
tggaccaaga cccagagagg acagagtggt tgtcccagct atagttacta aactactcac   5058
ccaaagttgg gacctcactg gcttctcttt acttcatcat ggatttcacc atcccaaggc   5118
agtctgagag gagctaaaga gtatcagccc atatttatta agcactttat gctccttggc   5178
acagcaggtg atgtgtaatt tatgcaagct ccctctccag ctaggactca ggatattagt   5238
caatgagcca tcaaaaggaa aaaaaaaaaa acctatctta ttttcatctg tttcatacct   5298
tgtctggggt ctaatgacga tggcaacagg gtagacatgg gaagacaggg tagaaaaggg   5358
tgcccgctct ttggggtcta gagatgagcc ctgggtctct aaaatggctc tcttagaagt   5418
tgtatgtgca aattatggtc tgtgtgctta ggtcgtgcac acctgccgga gccggtcaca   5478
gctgggcaga cgatgaatag ctgctttggg agagcagagc atgctagcca cttaattctc   5538
tgaccgggcc agcatcatgg gtacctgctc ccctgtgtac cccatcctta aggttttctg   5598
tctgatgaga ctggaggccc agtgcaatcc ccactgagac agcctgcagc ccactgtggc   5658
tcttggtgca ctcaccagcc aggactagac aagtaggaaa gggcttctag ccacactgga   5718 gaaaagaaa atcaggtagg gctggccaaa gacatctttg tccattcgca aaagctcttg   5778
tcggctgcag tgtgtaagtc aggcgatgag acagaggcta ccagagaaac ggatgagaac   5838
agcagcctga ggtttctcat ccagatatcc agcaattggg gggtggggga agaccataga   5898
tggtcctgta ttattccgat tttaataatc taattcgtga tcattaagag actttagtaa   5958
atgtcccttt tcccacaaaa gtaaagaaaa gctatcggga ttctctggtt ctgcttaaag   6018
acttagcttt ggagcctatg aaagttgatc agccagg                            6055

<210> SEQ ID NO 11
<211> LENGTH: 21
<212> TYPE: DNA
<213> ORGANISM: Artificial Sequence
<220> FEATURE:
<223> OTHER INFORMATION: PCR Primer

<400> SEQUENCE: 11
caatgtggag agccgagaca a                                               21

<210> SEQ ID NO 12
<211> LENGTH: 23
<212> TYPE: DNA
<213> ORGANISM: Artificial Sequence
<220> FEATURE:
<223> OTHER INFORMATION: PCR Primer

<400> SEQUENCE: 12
gaggtgttga aagactggaa cga                                             23

<210> SEQ ID NO 13
<211> LENGTH: 25
<212> TYPE: DNA
<213> ORGANISM: Artificial Sequence
<220> FEATURE:
<223> OTHER INFORMATION: PCR Probe

<400> SEQUENCE: 13
acacctgtcg cgtgaagagt gggtc                                           25

<210> SEQ ID NO 14
<211> LENGTH: 20
<212> TYPE: DNA
<213> ORGANISM: Artificial Sequence
<220> FEATURE:
```

<223> OTHER INFORMATION: PCR Primer

<400> SEQUENCE: 14
ggcaaattca acggcacagt                                                    20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
gggtctcgct cctggaagat                                                    20

<210> SEQ ID NO 16
<211> LENGTH: 27
<212> TYPE: DNA
<213> ORGANISM: Artificial Sequence
<220> FEATURE:
<223> OTHER INFORMATION: PCR Probe

<400> SEQUENCE: 16
aaggccgaga atgggaagct tgtcatc                                            27

<210> SEQ ID NO 17
<211> LENGTH: 1745
<212> TYPE: DNA
<213> ORGANISM: Homo sapiens
<220> FEATURE:

<400> SEQUENCE: 17
gtggcaactt tgggttaccc aaccttccta ggcggggagg tagtccagtc cttcaggaag        60
agtctctggc tccgttcaag agccatcaca gtcccttgta ttacatccct ctgacgggtt       120
ccaataggac tattttttcaa atctgcggta tttacagaga caagactggg ctgctccgtg      180
cagccaggac gacttcagcc tttgaggtaa tggagacata attgaggaac aacgtggaat       240
tagtgtcata gcaaatgatc tagggcctca agttaatttc agccggttgt ggtcagagtc       300
actcatcttg agtagcaagc tgccaccaga aagatttctt tttcgagcat ttagggaata       360
aagttcaagt gccctgcgct tccaagttgc aggagcagtt tcacgcctca gcttttttaaa      420 ggtatcataa tgttattcct tgttttgctt ctaggaagca aagactgag gaaatgactt       480 gggcgggtgc atcaatgcgg ccgaaaaaga cacggacacg ctcccctggg acctgagctg      540
gttcgcagtc ttcccaaagg tgccaagcaa gcgtcagttc ccctcaggcg ctccaggttc      600
agtgccttgt gccagggtc tccggtgcct tcctagactt ctcgggacag tctgaagggg       660
tcaggagcgg cgggacagcg cgggaagagc aggcaagggg agacagccgg actgcgcctc      720
agtcctccgt gccaagaaca ccgtcgcgga ggcgcggcca gcttcccttg gatcggactt      780
tccgccccta gggccaggcg gcggagcttc agccttgtcc cttccccagt ttcgggcggc      840
ccccagagct gagtaagccg ggtggaggga gtctgcaagg atttcctgag cgcgatgggc      900
aggaggaggg gcaagggcaa gagggcgcgg agcaaagacc ctgaacctgc cggggccgcg      960 ctccccgggcc cgcgtcgcca gcacctcccc acgcgcgctc ggccccgggc cacccgccct    1020
cgtcggcccc cgcccctctc cgtagccgca gggaagcgag cctgggagga agaagagggt    1080
aggtggggag gcggatgagg ggtggggggac cccttgacgt caccagaagg aggtgccggg    1140
gtaggaagtg ggctggggaa aggttataaa tcgcccccgc cctcggctgc tcttcatcga    1200

-continued

| | |
|---|---|
| ggtccgcggg aggctcggag cgcgccaggc ggacactcct ctcggctcct ccccggcagc | 1260 |
| ggcggcggct cggagcgggc tccggggctc gggtgcagcg gccagcgggc gcctggcggc | 1320 |
| gaggattacc cggggaagtg gttgtctcct ggctggagcc gcgagacggg cgctcagggc | 1380 |
| gcggggccgg cggcggcgaa cgagaggacg gactctggcg gccgggtctt tggccgcggg | 1440 |
| gagcgcgggc accgggcgag caggccgcgt cgcgctcacc atggtcagct actgggacac | 1500 |
| cggggtcctg ctgtgcgcgc tgctcagctg tctgcttctc acaggtgagg cgcggctggg | 1560 |
| ggccggggcc tgaggcgggc tgcgatgggg cggccggagg gcagagcctc cgaggccagg | 1620 |
| gcggggtgca cgcggggaga cgaggctgta gcccggagaa gctggctacg gcgagaacct | 1680 |
| gggacactag ttgcagcggg cacgcttggg gccgctgcgc cctttctccg agggagcgcc | 1740 |
| tcgag | 1745 |

<210> SEQ ID NO 18
<211> LENGTH: 530
<212> TYPE: DNA
<213> ORGANISM: Homo sapiens
<220> FEATURE:

<400> SEQUENCE: 18

| | |
|---|---|
| cagctggaga aagatctcat cttggcagct caggataaaa gactgtgggg aaagtttgcc | 60 |
| cactggtaaa tcttagataa ccagcttcgc tgatcaaata gtagcccagt ggattcagac | 120 |
| catttcttga ctttgagggc ttggggacct gtatttgtag agaggctctt catgtttatg | 180 |
| gtaactctgt gtgcaccgag agtgctccct tcacagcatg tgaaatggat tcccaaatta | 240 |
| agataatgac actgacaggt gtaggaaatt agttggttag gttaaggaaa tgcattgatt | 300 |
| atgcaactgt tttattatag tgcattcatc gggacctggc agcgagaaac attcttttat | 360 |
| ctgagaacaa cgtggtgaag atttgtgatt ttggccttgc ccgggatatt tataagaacc | 420 |
| ccgattatgt gagaaaagga gatgtaagtc agtttgatgt ttatttgact catgtgtgtc | 480 |
| ctatcacttt taaaccacag acttggtaaa tatttacact tcctcagctg | 530 |

<210> SEQ ID NO 19
<211> LENGTH: 2651
<212> TYPE: DNA
<213> ORGANISM: Homo sapiens
<220> FEATURE:
<221> NAME/KEY: CDS
<222> LOCATION: (250)...(2313)

<400> SEQUENCE: 19

| | |
|---|---|
| gcggacactc ctctcggctc ctccccggca gcggcggcgg ctcggagcgg gctccggggc | 60 |
| tcgggtgcag cggccagcgg gcctggcggc gaggattacc cggggaagtg gttgtctcct | 120 |
| ggctggagcc gcgagacggg cgctcagggc gcggggccgg cggcggcgaa cgagaggacg | 180 |
| gactctggcg gccgggtcgt tggccggggg agcgcgggca ccgggcgagc aggccgcgtc | 240 |

| | | |
|---|---|---|
| gcgctcacc atg gtc agc tac tgg gac acc ggg gtc ctg ctg tgc gcg ctg | | 291 |
| Met Val Ser Tyr Trp Asp Thr Gly Val Leu Leu Cys Ala Leu | | |
| 1 5 10 | | |

| | | |
|---|---|---|
| ctc agc tgt ctg ctt ctc aca gga tct agt tca ggt tca aaa tta aaa | | 339 |
| Leu Ser Cys Leu Leu Leu Thr Gly Ser Ser Ser Gly Ser Lys Leu Lys | | |
| 15 20 25 30 | | |

| | | |
|---|---|---|
| gat cct gaa ctg agt tta aaa ggc acc cag cac atc atg caa gca ggc | | 387 |
| Asp Pro Glu Leu Ser Leu Lys Gly Thr Gln His Ile Met Gln Ala Gly | | |
| 35 40 45 | | |

| | | |
|---|---|---|
| cag aca ctg cat ctc caa tgc agg ggg gaa gca gcc cat aaa tgg tct | | 435 |

```
                Gln Thr Leu His Leu Gln Cys Arg Gly Glu Ala Ala His Lys Trp Ser
                            50                  55                  60 ttg cct gaa atg gtg agt aag gaa agc gaa agg ctg agc ata act aaa       483
Leu Pro Glu Met Val Ser Lys Glu Ser Glu Arg Leu Ser Ile Thr Lys
            65                  70                  75 tct gcc tgt gga aga aat ggc aaa caa ttc tgc agt act tta acc ttg       531
Ser Ala Cys Gly Arg Asn Gly Lys Gln Phe Cys Ser Thr Leu Thr Leu
        80                  85                  90 aac aca gct caa gca aac cac act ggc ttc tac agc tgc aaa tat cta       579
Asn Thr Ala Gln Ala Asn His Thr Gly Phe Tyr Ser Cys Lys Tyr Leu
 95                 100                 105                 110 gct gta cct act tca aag aag aag gaa aca gaa tct gca atc tat ata       627
Ala Val Pro Thr Ser Lys Lys Lys Glu Thr Glu Ser Ala Ile Tyr Ile
                115                 120                 125 ttt att agt gat aca ggt aga cct ttc gta gag atg tac agt gaa atc       675
Phe Ile Ser Asp Thr Gly Arg Pro Phe Val Glu Met Tyr Ser Glu Ile
            130                 135                 140 ccc gaa att ata cac atg act gaa gga agg gag ctc gtc att ccc tgc       723
Pro Glu Ile Ile His Met Thr Glu Gly Arg Glu Leu Val Ile Pro Cys
        145                 150                 155 cgg gtt acg tca cct aac atc act gtt act tta aaa aag ttt cca ctt       771
Arg Val Thr Ser Pro Asn Ile Thr Val Thr Leu Lys Lys Phe Pro Leu
    160                 165                 170 gac act ttg atc cct gat gga aaa cgc ata atc tgg gac agt aga aag       819
Asp Thr Leu Ile Pro Asp Gly Lys Arg Ile Ile Trp Asp Ser Arg Lys
175                 180                 185                 190 ggc ttc atc ata tca aat gca acg tac aaa gaa ata ggg ctt ctg acc       867
Gly Phe Ile Ile Ser Asn Ala Thr Tyr Lys Glu Ile Gly Leu Leu Thr
                195                 200                 205 tgt gaa gca aca gtc aat ggg cat ttg tat aag aca aac tat ctc aca       915
Cys Glu Ala Thr Val Asn Gly His Leu Tyr Lys Thr Asn Tyr Leu Thr
            210                 215                 220 cat cga caa acc aat aca atc ata gat gtc caa ata agc aca cca cgc       963
His Arg Gln Thr Asn Thr Ile Ile Asp Val Gln Ile Ser Thr Pro Arg
        225                 230                 235 cca gtc aaa tta ctt aga ggc cat act ctt gtc ctc aat tgt act gct      1011
Pro Val Lys Leu Leu Arg Gly His Thr Leu Val Leu Asn Cys Thr Ala
    240                 245                 250 acc act ccc ttg aac acg aga gtt caa atg acc tgg agt tac cct gat      1059
Thr Thr Pro Leu Asn Thr Arg Val Gln Met Thr Trp Ser Tyr Pro Asp
255                 260                 265                 270 gaa aaa aat aag aga gct tcc gta agg cga cga att gac caa agc aat      1107
Glu Lys Asn Lys Arg Ala Ser Val Arg Arg Ile Asp Gln Ser Asn
                275                 280                 285 tcc cat gcc aac ata ttc tac agt gtt ctt act att gac aaa atg cag      1155
Ser His Ala Asn Ile Phe Tyr Ser Val Leu Thr Ile Asp Lys Met Gln
            290                 295                 300 aac aaa gac aaa gga ctt tat act tgt cgt gta agg agt gga cca tca      1203
Asn Lys Asp Lys Gly Leu Tyr Thr Cys Arg Val Arg Ser Gly Pro Ser
        305                 310                 315 ttc aaa tct gtt aac acc tca gtg cat ata tat gat aaa gca ttc atc      1251
Phe Lys Ser Val Asn Thr Ser Val His Ile Tyr Asp Lys Ala Phe Ile
    320                 325                 330 act gtg aaa cat cga aaa cag cag gtg ctt gaa acc gta gct ggc aag      1299
Thr Val Lys His Arg Lys Gln Gln Val Leu Glu Thr Val Ala Gly Lys
335                 340                 345                 350 cgg tct tac cgg ctc tct atg aaa gtg aag gca ttt ccc tcg ccg gaa      1347
Arg Ser Tyr Arg Leu Ser Met Lys Val Lys Ala Phe Pro Ser Pro Glu
                355                 360                 365
```

-continued

```
gtt gta tgg tta aaa gat ggg tta cct gcg act gag aaa tct gct cgc    1395
Val Val Trp Leu Lys Asp Gly Leu Pro Ala Thr Glu Lys Ser Ala Arg
        370                 375                 380 tat ttg act cgt ggc tac tcg tta att atc aag gac gta act gaa gag    1443
Tyr Leu Thr Arg Gly Tyr Ser Leu Ile Ile Lys Asp Val Thr Glu Glu
            385                 390                 395 gat gca ggg aat tat aca atc ttg ctg agc ata aaa cag tca aat gtg    1491
Asp Ala Gly Asn Tyr Thr Ile Leu Leu Ser Ile Lys Gln Ser Asn Val
400                 405                 410 ttt aaa aac ctc act gcc act cta att gtc aat gtg aaa ccc cag att    1539
Phe Lys Asn Leu Thr Ala Thr Leu Ile Val Asn Val Lys Pro Gln Ile
415                 420                 425                 430 tac gaa aag gcc gtg tca tcg ttt cca gac ccg gct ctc tac cca ctg    1587
Tyr Glu Lys Ala Val Ser Ser Phe Pro Asp Pro Ala Leu Tyr Pro Leu
                435                 440                 445 ggc agc aga caa atc ctg act tgt acc gca tat ggt atc cct caa cct    1635
Gly Ser Arg Gln Ile Leu Thr Cys Thr Ala Tyr Gly Ile Pro Gln Pro
            450                 455                 460 aca atc aag tgg ttc tgg cac ccc tgt aac cat aat cat tcc gaa gca    1683
Thr Ile Lys Trp Phe Trp His Pro Cys Asn His Asn His Ser Glu Ala
465                 470                 475 agg tgt gac ttt tgt tcc aat aat gaa gag tcc ttt atc ctg gat gct    1731
Arg Cys Asp Phe Cys Ser Asn Asn Glu Glu Ser Phe Ile Leu Asp Ala
480                 485                 490 gac agc aac atg gga aac aga att gag agc atc act cag cgc atg gca    1779
Asp Ser Asn Met Gly Asn Arg Ile Glu Ser Ile Thr Gln Arg Met Ala
495                 500                 505                 510 ata ata gaa gga aag aat aag atg gct agc acc ttg gtt gtg gct gac    1827
Ile Ile Glu Gly Lys Asn Lys Met Ala Ser Thr Leu Val Val Ala Asp
                515                 520                 525 tct aga att tct gga atc tac att tgc ata gct tcc aat aaa gtt ggg    1875
Ser Arg Ile Ser Gly Ile Tyr Ile Cys Ile Ala Ser Asn Lys Val Gly
            530                 535                 540 act gtg gga aga aac ata agc ttt tat atc aca gat gtg cca aat ggg    1923
Thr Val Gly Arg Asn Ile Ser Phe Tyr Ile Thr Asp Val Pro Asn Gly
545                 550                 555 ttt cat gtt aac ttg gaa aaa atg ccg acg gaa gga gag gac ctg aaa    1971
Phe His Val Asn Leu Glu Lys Met Pro Thr Glu Gly Glu Asp Leu Lys
560                 565                 570 ctg tct tgc aca gtt aac aag ttc tta tac aga gac gtt act tgg att    2019
Leu Ser Cys Thr Val Asn Lys Phe Leu Tyr Arg Asp Val Thr Trp Ile
575                 580                 585                 590 tta ctg cgg aca gtt aat aac aga aca atg cac tac agt att agc aag    2067
Leu Leu Arg Thr Val Asn Asn Arg Thr Met His Tyr Ser Ile Ser Lys
                595                 600                 605 caa aaa atg gcc atc act aag gag cac tcc atc act ctt aat ctt acc    2115
Gln Lys Met Ala Ile Thr Lys Glu His Ser Ile Thr Leu Asn Leu Thr
            610                 615                 620 atc atg aat gtt tcc ctg caa gat tca ggc acc tat gcc tgc aga gcc    2163
Ile Met Asn Val Ser Leu Gln Asp Ser Gly Thr Tyr Ala Cys Arg Ala
625                 630                 635 agg aat gta tac aca ggg gaa gaa atc ctc cag aag aaa gaa att aca    2211
Arg Asn Val Tyr Thr Gly Glu Glu Ile Leu Gln Lys Lys Glu Ile Thr
640                 645                 650 atc aga ggt gag cac tgc aac aaa aag gct gtt ttc tct cgg atc tcc    2259
Ile Arg Gly Glu His Cys Asn Lys Lys Ala Val Phe Ser Arg Ile Ser
655                 660                 665                 670 aaa ttt aaa agc aca agg aat gat tgt acc aca caa agt aat gta aaa    2307
Lys Phe Lys Ser Thr Arg Asn Asp Cys Thr Thr Gln Ser Asn Val Lys
                675                 680                 685
```

```
cat taa aggactcatt aaaaagtaac agttgtctca tatcatcttg atttattgtc      2363
His actgttgcta actttcaggc tcggaggaga tgctcctccc aaaatgagtt cggagatgat   2423
agcagtaata atgagacccc cgggctccag ctctgggccc ccattcagg ccgaggggc     2483 tgctccgggg ggccgacttg gtgcacgttt ggatttggag gatccctgca ctgccttctc   2543
tgtgtttgtt gctcttgctg ttttctcctg cctgataaac aacaacttgg gatgatcctt  2603
tccattttga tgccaacctc ttttttatttt taagcggcgc cctatagt              2651
```

<210> SEQ ID NO 20
<211> LENGTH: 751
<212> TYPE: DNA
<213> ORGANISM: Homo sapiens
<220> FEATURE:
<221> NAME/KEY: unsure
<222> LOCATION: 124
<223> OTHER INFORMATION: unknown
<221> NAME/KEY: unsure
<222> LOCATION: 180
<223> OTHER INFORMATION: unknown
<223> OTHER INFORMATION:

<400> SEQUENCE: 20

```
ggggaggaat cctcagaaga aagaagtgca atcagagtca ggagccacat ccctcctcca    60
aacgtcagtg atacacagtg gcatcagcag ttccacactt tagactgtca tgctaatggt  120
gtcnccgagc ctcagatcac ttggtttaaa acaaccaca aaatacaacg agagcctgan   180
ctgtatacat caacgtcacc atcgtcatcg tcatcatcac cattgtcatc atcatcatca   240
tcgtcatcat catcatcatc atagctatca tcattatcat catcatcatc atcatcatca   300
tagctaccat ttattgaaaa ctattatgtg tcaacttcaa agaacttatc ctttagttgg   360
agagccaaga caatcataac aataacaaat ggccgggcat ggtggctcac gcctgtaatc   420
ccagcacttt gggaggccaa ggcaggtgga tcatttgagg tcaggagttc aagaccagcc   480
tgaccaagat ggtgaaatgc tgtctctatt aaaaatacaa aattagccgg gcatggtggc   540
tcatgcctgt aatgccagct actcgggagg ctgagacagg agaatcactt gaacccagga   600
ggcagaggtt gcacggaccc gagatcgtgt actgcactcc agcctgggca acaagagcga   660
aactccgtct caaaaaacaa ataaataaat aaataaataa acagacaaaa ttcactttt    720 attctattaa acttaacata catgcattaa a                                  751
```

<210> SEQ ID NO 21
<211> LENGTH: 338
<212> TYPE: DNA
<213> ORGANISM: Homo sapiens
<220> FEATURE:
<221> NAME/KEY: CDS
<222> LOCATION: (154)...(198)

<400> SEQUENCE: 21

```
gagagcatca ctcagcgcat ggcaataata gaaggaaaga ataagatggc tagcaccttg    60
gttgtggctg actctagaat ttctggaatc tacatttgca tagcttccaa taaagttggg   120
actgtgggaa gaaacataag ctttttatatc aca gaa ttg tca aac ttt gag tgc   174
                                    Glu Leu Ser Asn Phe Glu Cys
                                    1               5 ctt cat cct tgc tct cag gaa tag aactctacct catcggatct catgtgccaa    228
Leu His Pro Cys Ser Gln Glu
        10
```

```
atgggtttca tgttaacttg gaaaaaatgc cgacggaagg agaggacctg aaactgtctt    288
gcacagttaa caagttctta tacagagacg ttacttggat tttactgcgg              338
```

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22

```
gctgaccatg gtgagcgcga                                                20
```

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23

```
aggatctttt aattttgaac                                                20
```

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24

```
gtgccttttta aactcagttc                                               20
```

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25

```
tgctgggtgc cttttaaact                                                20
```

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26

```
gtttgcttga gctgtgttca                                                20
```

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27

```
ccttcttctt tgaagtaggt                                                20
```

<210> SEQ ID NO 28
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 28
cgaaaggtct acctgtatca                                              20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
gatatgatga agccctttct                                              20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
actgttgctt cacaggtcag                                              20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
gcagtacaat tgaggacaag                                              20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
tttggtcaat tcgtcgcctt                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
cgacaagtat aaagtccttt                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
```

```
acagatttga atgatggtcc                                          20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
cagtgatgaa tgctttatca                                          20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
ttgataatta acgagtagcc                                          20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
actgttttat gctcagcaag                                          20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
gtgaggtttt taaacacatt                                          20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
gagtggcagt gaggttttta                                          20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
gacaattaga gtggcagtga                                          20

<210> SEQ ID NO 41
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 41
ttcacattga caattagagt                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
gctgcccagt gggtagagag                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
ttgtctgctg cccagtgggt                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
ccacttgatt gtaggttgag                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
atgttgctgt cagcatccag                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
gatgctctca attctgtttc                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
catgcgctga gtgatgctct                                               20
```

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
ccaactttat tggaagctat                                           20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
acagtttcag gtcctctcct                                           20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
ccgcagtaaa atccaagtaa                                           20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
ttgcttgcta atactgtagt                                           20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
gctctgcagg cataggtgcc                                           20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
ttcctggctc tgcaggcata                                           20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 54
ttcccctgtg tatacattcc                                          20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
ctggaggatt tcttcccctg                                          20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
cctggtccta aaataattcc                                          20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
ctttcaataa acagcgtgct                                          20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
gtgactcttt caataaacag                                          20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
cctcttctgt gactctttca                                          20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
tcccacttgc tggcatcata                                          20

<210> SEQ ID NO 61
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
gcaaactccc acttgctggc                                            20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
gtgatttctt aatgccaaat                                            20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
ttcacagcca cagtccggca                                            20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
gtcatcagag ctttgtactc                                            20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
ttgcttggtg caggctccca                                            20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
ggccctcctt gcttggtgca                                            20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
```
atcagaggcc ctccttgctt                               20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
atcaccatca gaggccctcc                               20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
tttgctcttg aggtagttgg                               20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
gtcacgtttg ctcttgaggt                               20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
aataagtcac gtttgctctt                               20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
tccatgcctc tggccacttg                               20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
cgatgaatgc actttctgga                               20

<210> SEQ ID NO 74
<211> LENGTH: 20
<212> TYPE: DNA

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
caggtcccga tgaatgcact                                         20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
tcgctgccag gtcccgatga                                         20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
atgtttctcg ctgccaggtc                                         20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
ttcttataaa tatcccgggc                                         20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78 gattcgggagccatccattt                                          20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79 gtagtctttaccatcctgtt                                          20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80 gggatgtagtctttaccatc                                          20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81 gattctttccaggctcatga         20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82 ggttttgattctttccaggc         20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83 tcaaacatggaggtggcatt         20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84 gtcaaactctagatgggtgg         20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85 ttacattcttgttagtcaaa         20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86 ttgcataaatagcatcaaac         20

<210> SEQ ID NO 87
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 87 agtcttccacaaaagccgct					20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88 atgaggctagcgagtatctg					20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89 cagggcacttgaactttatt					20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90 gcagcggccccaagcgtgcc					20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91 gagcctctctacaaatacag					20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92 tccgagagaaaacagccttt					20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93 gagacaactgttactttta					20

-continued

```
<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94 gggaggagcatctcctccga                                                    20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95 agcagcccctcggcctgaa                                                     20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96 ttggcatcaaaatggaaagg                                                    20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97 tggtgatgatgacgatgacg                                                    20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98 caccatgcccggctaatttt                                                    20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99 ccgatgaggtagagttctat                                                    20

<210> SEQ ID NO 100
<211> LENGTH: 3394
<212> TYPE: DNA
<213> ORGANISM: Mus musculus
<220> FEATURE:
<221> NAME/KEY: CDS
<222> LOCATION: (252)...(2318)
```

-continued

```
<400> SEQUENCE: 100
agcgcggagg cggacactcc cgggaggtag tgctagtggt ggtggctgct gctcggagcg        60
ggctccggga ctcaagcgca gcggctagcg gacgcgggac ggcgtggatc cccccacacc       120 accccctcg gctgcaggcg cggagaaggg ctctcgcggc gccaagcaga agcaggaggg        180
gaccggctcg agcgtgccgc gtcggcctcg gagagcgcgg gcaccggcca acaggccgcg       240
tcttgctcac c atg gtc agc tgc tgg gac acc gcg gtc ttg cct tac gcg       290
            Met Val Ser Cys Trp Asp Thr Ala Val Leu Pro Tyr Ala
              1               5                  10 ctg ctc ggg tgt ctg ctt ctc aca gga tat ggc tca ggg tcg aag tta       338
Leu Leu Gly Cys Leu Leu Leu Thr Gly Tyr Gly Ser Gly Ser Lys Leu
     15                  20                  25 aaa gtg cct gaa ctg agt tta aaa ggc acc cag cat gtc atg caa gca       386
Lys Val Pro Glu Leu Ser Leu Lys Gly Thr Gln His Val Met Gln Ala
 30                  35                  40                  45 ggc cag act ctc ttt ctc aag tgc aga ggg gag gca gcc cac tca tgg       434
Gly Gln Thr Leu Phe Leu Lys Cys Arg Gly Glu Ala Ala His Ser Trp
                 50                  55                  60 tct ctg ccc acg acc gtg agc cag gag gac aaa agg ctg agc atc act       482
Ser Leu Pro Thr Thr Val Ser Gln Glu Asp Lys Arg Leu Ser Ile Thr
             65                  70                  75 ccc cca tcg gcc tgt ggg agg gat aac agg caa ttc tgc agc acc ttg       530
Pro Pro Ser Ala Cys Gly Arg Asp Asn Arg Gln Phe Cys Ser Thr Leu
         80                  85                  90 acc ttg gac acg gcg cag gcc aac cac acg ggc ctc tac acc tgt aga       578
Thr Leu Asp Thr Ala Gln Ala Asn His Thr Gly Leu Tyr Thr Cys Arg
     95                 100                 105 tac ctc cct aca tct act tcg aag aaa aag aaa gcg gaa tct tca atc       626
Tyr Leu Pro Thr Ser Thr Ser Lys Lys Lys Lys Ala Glu Ser Ser Ile
110                 115                 120                 125 tac ata ttt gtt agt gat gca ggg agt cct ttc ata gag atg cac act       674
Tyr Ile Phe Val Ser Asp Ala Gly Ser Pro Phe Ile Glu Met His Thr
                130                 135                 140 gac ata ccc aaa ctt gtg cac atg acg gaa gga aga cag ctc atc atc       722
Asp Ile Pro Lys Leu Val His Met Thr Glu Gly Arg Gln Leu Ile Ile
            145                 150                 155 ccc tgc cgg gtg acg tca ccc aac gtc aca gtc acc cta aaa aag ttt       770
Pro Cys Arg Val Thr Ser Pro Asn Val Thr Val Thr Leu Lys Lys Phe
        160                 165                 170 cca ttt gat act ctt acc cct gat ggg caa aga ata aca tgg gac agt       818
Pro Phe Asp Thr Leu Thr Pro Asp Gly Gln Arg Ile Thr Trp Asp Ser
    175                 180                 185 agg aga ggc ttt ata ata gca aat gca acg tac aaa gag ata gga ctg       866
Arg Arg Gly Phe Ile Ile Ala Asn Ala Thr Tyr Lys Glu Ile Gly Leu
190                 195                 200                 205 ctg aac tgc gaa gcc acc gtc aac ggg cac ctg tac cag aca aac tat       914
Leu Asn Cys Glu Ala Thr Val Asn Gly His Leu Tyr Gln Thr Asn Tyr
                210                 215                 220 ctg acc cat cgg cag acc aat aca atc cta gat gtc caa ata cgc ccg       962
Leu Thr His Arg Gln Thr Asn Thr Ile Leu Asp Val Gln Ile Arg Pro
            225                 230                 235 ccg agc cca gtg aga ctg ctc cac ggg cag act ctt gtc ctc aac tgc      1010
Pro Ser Pro Val Arg Leu Leu His Gly Gln Thr Leu Val Leu Asn Cys
        240                 245                 250 acc gcc acc acg gag ctc aat acg agg gtg caa atg agc tgg aat tac      1058
Thr Ala Thr Thr Glu Leu Asn Thr Arg Val Gln Met Ser Trp Asn Tyr
    255                 260                 265
```

```
cct ggt aaa gca act aag aga gca tct ata agg cag cgg att gac cgg   1106
Pro Gly Lys Ala Thr Lys Arg Ala Ser Ile Arg Gln Arg Ile Asp Arg
270             275                 280                 285 agc cat tcc cac aac aat gtg ttc cac agt gtt ctt aag atc aac aat   1154
Ser His Ser His Asn Asn Val Phe His Ser Val Leu Lys Ile Asn Asn
                290                 295                 300 gtg gag agc cga gac aag ggg ctc tac acc tgt cgc gtg aag agt ggg   1202
Val Glu Ser Arg Asp Lys Gly Leu Tyr Thr Cys Arg Val Lys Ser Gly
            305                 310                 315 tcc tcg ttc cag tct ttc aac acc tcc gtg cat gtg tat gaa aaa gga   1250
Ser Ser Phe Gln Ser Phe Asn Thr Ser Val His Val Tyr Glu Lys Gly
        320                 325                 330 ttc atc agt gtg aaa cat cgg aag cag ccg gtg cag gaa acc aca gca   1298
Phe Ile Ser Val Lys His Arg Lys Gln Pro Val Gln Glu Thr Thr Ala
335                 340                 345 gga aga cgg tcc tat cgg ctg tcc atg aaa gtg aag gcc ttc ccc tcc   1346
Gly Arg Arg Ser Tyr Arg Leu Ser Met Lys Val Lys Ala Phe Pro Ser
350                 355                 360                 365 cca gaa atc gta tgg tta aaa gat ggc tcg cct gca aca ttg aag tct   1394
Pro Glu Ile Val Trp Leu Lys Asp Gly Ser Pro Ala Thr Leu Lys Ser
                370                 375                 380 gct cgc tat ttg gta cat ggc tac tca tta att atc aaa gat gtg aca   1442
Ala Arg Tyr Leu Val His Gly Tyr Ser Leu Ile Ile Lys Asp Val Thr
            385                 390                 395 acc gag gat gca ggg gac tat acg atc ttg ctg gga ata aag cag tca   1490
Thr Glu Asp Ala Gly Asp Tyr Thr Ile Leu Leu Gly Ile Lys Gln Ser
        400                 405                 410 agg cta ttt aaa aac ctc act gcc act ctc att gta aac gtg aaa cct   1538
Arg Leu Phe Lys Asn Leu Thr Ala Thr Leu Ile Val Asn Val Lys Pro
415                 420                 425 cag atc tac gaa aag tcc gtg tcc tcg ctt cca agc cca cct ctc tat   1586
Gln Ile Tyr Glu Lys Ser Val Ser Ser Leu Pro Ser Pro Pro Leu Tyr
430                 435                 440                 445 ccg ctg ggc agc aga caa gtc ctc act tgc acc gtg tat ggc atc cct   1634
Pro Leu Gly Ser Arg Gln Val Leu Thr Cys Thr Val Tyr Gly Ile Pro
                450                 455                 460 cgg cca aca atc acg tgg ctc tgg cac ccc tgt cac cac aat cac tcc   1682
Arg Pro Thr Ile Thr Trp Leu Trp His Pro Cys His His Asn His Ser
            465                 470                 475 aaa gaa agg tat gac ttc tgc act gag aat gaa gaa tcc ttt atc ctg   1730
Lys Glu Arg Tyr Asp Phe Cys Thr Glu Asn Glu Glu Ser Phe Ile Leu
        480                 485                 490 gat ccc agc agc aac tta gga aac aga att gag agc atc tct cag cgc   1778
Asp Pro Ser Ser Asn Leu Gly Asn Arg Ile Glu Ser Ile Ser Gln Arg
495                 500                 505 atg acg gtc ata gaa gga aca aat aag acg gtt agc aca ttg gtg gtg   1826
Met Thr Val Ile Glu Gly Thr Asn Lys Thr Val Ser Thr Leu Val Val
510                 515                 520                 525 gct gac tct cag acc cct gga atc tac agc tgc cgg gcc ttc aat aaa   1874
Ala Asp Ser Gln Thr Pro Gly Ile Tyr Ser Cys Arg Ala Phe Asn Lys
                530                 535                 540 ata ggg act gtg gaa aga aac ata aaa ttt tac gtc aca gat gtg ccg   1922
Ile Gly Thr Val Glu Arg Asn Ile Lys Phe Tyr Val Thr Asp Val Pro
            545                 550                 555 aat ggc ttt cac gtt tcc ttg gaa aag atg cca gcc gaa gga gag gac   1970
Asn Gly Phe His Val Ser Leu Glu Lys Met Pro Ala Glu Gly Glu Asp
        560                 565                 570 ctg aaa ctg tcc tgt gtg gtc aat aaa ttc ctg tac aga gac att acc   2018
Leu Lys Leu Ser Cys Val Val Asn Lys Phe Leu Tyr Arg Asp Ile Thr
575                 580                 585
```

-continued

```
tgg att ctg cta cgg aca gtt aac aac aga acc atg cac cat agt atc    2066
Trp Ile Leu Leu Arg Thr Val Asn Asn Arg Thr Met His His Ser Ile
590                 595                 600                 605 agc aag caa aaa atg gcc acc act caa gat tac tcc atc act ctg aac    2114
Ser Lys Gln Lys Met Ala Thr Thr Gln Asp Tyr Ser Ile Thr Leu Asn
            610                 615                 620 ctt gtc atc aag aac gtg tct cta gaa gac tcg ggc acc tat gcg tgc    2162
Leu Val Ile Lys Asn Val Ser Leu Glu Asp Ser Gly Thr Tyr Ala Cys
            625                 630                 635 aga gcc agg aac ata tac aca ggg gaa gac atc ctt cgg aag aca gaa    2210
Arg Ala Arg Asn Ile Tyr Thr Gly Glu Asp Ile Leu Arg Lys Thr Glu
            640                 645                 650 gtt ctc gtt aga ggt gag cac tgc ggc aaa aag gcc att ttc tct cgg    2258
Val Leu Val Arg Gly Glu His Cys Gly Lys Lys Ala Ile Phe Ser Arg
            655                 660                 665 atc tcc aaa ttt aaa agc agg agg aat gat tgt acc aca caa agt cat    2306
Ile Ser Lys Phe Lys Ser Arg Arg Asn Asp Cys Thr Thr Gln Ser His
670                 675                 680                 685 gtc aaa cat taa aggactcatt tgaaaagtaa cagttgtctc ttatcatctc        2358
Val Lys His agtttattgt tactgttgct aactttcagg cccagaggaa acgctcctcc caaaatgagt    2418
ttggacatga taacgtaata agaaagccca gtgccctctg cccggggtgc ccgctggccc    2478
gggggtgctc tgtgggccgc ccggtgtgtg tttggatttg aagatccctg tactctgttt    2538
cttttgtgtg tctgctcttc tgtcttctgc ttcatagcag caacctggga cgcatgtttt    2598
tcttccactc tgatgccaac ctctttgat atatatat atttttaagt tgtgaagctg      2658
aacaaactga ataatttaag caaatgctgg tttctgccaa agacggacat gaataagtta    2718
attttttttc cagcacagga tgcgtacagt tgaatttgga atctgtgtcg ggtgtctacc    2778
tggttttatt ttttactatt tcatttttg ctcttgattt gtaaatagtt cctggataac     2838
aagttataat gcttatttat ttgaaacttg gttgttttgt tgttttttt ttcttttcat     2898 gaagtatatt gatcttaaac tggagggttc taagatgggt cccagggct caagatgttg     2958 atgtcattcc gagagtaaag ctatgtccca atgtgaatta tgaaggtcca gcaggtctgc    3018
tccaccctcc tctgtccacc caggtaatta cacgtgtgtt tcctgctgtg ttagatgctg    3078
ttcctcattg tccttggctg gactgacagc ccctgactga cggcaaaagt gcagcaagcc    3138
ttcattataa acactcatgg cccctgggca ctgttttaaa gcccttcacc aagctttgat    3198
ggcattcaaa gatgtccaca acccatgtat ccaggatata aaggctattg tgagtggaga    3258
tttaatgcaa tcttcttaat gtctattgaa aaatctaccc atgagagaaa gaaagtcca    3318 ccttctctat atgcaaatgt tttatgggga ttaagaaatt gcaaaagcta agaaattaca    3378
aaaaaaaaaa aaaaaa                                                    3394
```

<210> SEQ ID NO 101
<211> LENGTH: 2648
<212> TYPE: DNA
<213> ORGANISM: Mus musculus
<220> FEATURE:

<400> SEQUENCE: 101

```
gatctttccc atcaatggta tctagaaaac ctctttcatg actgatttgg ttcgaagagt     60
cctactgtag cccattattc aactctgtta ccacttctgg ggaaagggtc ttagcccttt    120
attgtccata tcaaagtgaa gttgaaatgt ccaatgaaac agtttgtatc attttaaaat    180
```

```
tcttaataac aataataaca ataacaacca atgcaaccta caaagaaat attggtgtgg      240 aagttgttgg ctgtaaatta aaagtctggg cttttcaaa agagttggag aaacgtatcg      300
aaggccacag catataaacc ttagctactt caattacgag gccattaatc ttagataatt    360
gagcgatatt ttagcattgt taatgcacag cttaagttat agatggtttt ggctgtcggt    420
caaatacctg tctggcttca tgatcccata aagtcattgt gggatcattt ctggcaacaa    480
actcataagg atctccttga gtatttaaag acatcaaaat gccatttgaa acaacgcat     540 taaactaaac ctttggggac tgtacatgca acacttcccc caagttggta gttcccctcg    600
ctggtcttcc cctacaataa gccatgcccg tgtttctgtg ctcatggtgg gcttcatacc    660
cctctagaat cgtacacctc ctccacgttg tgtgtcttgg tttctgtcgg cctgctcagc    720
gcagcacctc cagcctcagt ggcgatgggt ttccaattgg caagctctcc ccagcccaaa    780
cacctgccat tgcttaaagg ggctgagcag acctcttaga agatgcgtgg gcgttaggat    840
agctcttagg ggagacaggg acagtttgac cgtgtgggtg tgtcaagacc atctgaggcc    900
ggagattcag ctgggagaat tataactacc tagtgcgggc catcctgcat gattcctgat    960
tggagagcaa tttgaggcgc cggaggcaga gggcaggaat actgaccccta gtggaagctt   1020 gtagagaaat cagaattggc tggggaagtc cgcaggtgag cttaggctca cagcggtctt    1080
tcccttctgc tagaccatga aggagaaaag gaatctcact tgccctggct cagaggctcc    1140
cggtgcccta gtagagctgc gggtggtggt ggcccagact ctcttaggaa tgaggcaact    1200
caggttgcgc aaccttccct accggaggtt tagtctagtc cttcaggaaa agcctctggt    1260
cccatttagg agccatttta tcacgggtat ctggcaggtt ctattgaggc tattttcaa    1320 acctgcagta tttacaggga caagactggg ctgctccggg gaggccggga cgacttcagc   1380
cttccagtta atggatgcat aattgaggaa caacgtggaa ttagtgtcat cgtaaatgat    1440
ctagtgtctc aagttaattt cacccgtttt ttgttccaag aacattcgag tcagtcatct    1500
tggctagccg gcttccacca aaaagatttg ttttccatcc agcgtttcag acctagagtt    1560
caagttcttg gccttacaa gttgcaggag cgtgtctcac gccttggctt ttttttttt    1620 tttttttttt tttttttaa ggtaacatgt tattccttgt tttgcttcta ggaagcagag    1680
ggttgaggaa atggcttggg cggtgcatt aatgcagccg aaaaagacac agactccctc    1740
ccttgggacc cgcgcggccc cgcgctcttt ccgaaggtgc ctggcaaggc gtccggttcc    1800
ctcggacgct ccgggtccaa gtgccttaag cggaggtct ctggcgcctt ccttcgctgt    1860
ctggcaacag tctggcgggg tcagggaccg gcgggaccgc tcgggagagg gctcgactgc    1920
gcctcgttcc tcggtgccag ggacaccgtc gcggaggcg cggccagctt ccctaggata    1980
agacttcccg ccccgggggc agggcggtgc acttagacgg tcccctcctc agtttcgggc    2040
ggtcaccaga gctgagtaag ctcggtggag ggagctgggt aaggattcc tgagagcgat   2100 gggcaggagg ggctggggca gcagagcaca gagcaaggac cctgaacctg cgaacctgtc    2160
cggcgacccg cgcgcctagc gccaccgcac gcgcgctctg gccccgggc tacccgccct    2220 cgccggcccc cgcccctccg ggaggaagaa gagggtaggt ggggaggcgg atgaggggtg    2280
ggggacccct tgacgtcact ggaaggaggt gcgggggtag gaagtgggct ggggaaaggt   2340
tataaatcgc ccccgccctc ggctgcactt cagcgaggtc cttgagaggc tcggagcgcg    2400
gtggcggaca ctcccgggag gtagtgctag tggtggtggc tgctgctcgg agcgggctcc    2460
gggactcaag cgcagcggct agcggacgcg ggacggcgag gatcccccca caccacccc    2520 ctcggctgca ggcgcggaga agggctctcg cggcgccaag cagaagcagg aggggaccgg    2580
```

```
ctcgagcggc tgcgccgtcg gcctcggaga gcgcgggcac cgggccaaca ggccgcgtct    2640
tgctcacc                                                              2648
```

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102

```
cagctgacca tggtgagcaa                                                 20
```

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103

```
tcctgtgaga agcagacacc                                                 20
```

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104

```
tctgcacttg agaaagagag                                                 20
```

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105

```
aggcccgtgt ggttggcctg                                                 20
```

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106

```
agccaaaacc atctataact                                                 20
```

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107

```
aaggactccc tgcatcacta                                                 20
```

<210> SEQ ID NO 108

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
taaagcctct cctactgtcc                                                     20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
acgttgcatt tgctattata                                                     20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
accaagacac acaacgtgga                                                     20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
tattggtctg ccgatgggtc                                                     20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
tttggacatc taggattgta                                                     20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
ttctaagagg tctgctcagc                                                     20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
```
ctcttagttg ctttaccagg    20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
gggaaggcct tcactttcat    20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
agtgaggact tgtctgctgc    20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
gagggatgcc atacacggtg    20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
actgactcga atgttcttgg    20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
gagagtcagc caccaccaat    20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
taatgtctct gtacaggaat    20

<210> SEQ ID NO 121
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 121
atgacaaggt tcagagtgat                                                   20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
ttcccctgtg tatatgttcc                                                   20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
tcctagggaa gctggccgcg                                                   20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
tcactgaggt tttgaagcag                                                   20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
ttgaaccaag tgatctgagg                                                   20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
aacagcgtgc tgtttcctgg                                                   20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
ggttggtggc tcggcaccta                                                   20
```

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
acaatcattc ctcctgcttt                                            20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
tgacttgtct gaggttcctt                                            20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
gttagaagga gccaaaagag                                            20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
tttacttcgg aagaagaccg                                            20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
atgtccaaac tcattttggg                                            20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
cggcaggtgg gtgatttctt                                            20

<210> SEQ ID NO 134
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 134
cagcttcaca acttaaaaat                                         20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
tggccgatgt gggtcaagat                                         20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
gttatccagg aactatttac                                         20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
taagcattat aacttgttat                                         20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
ctgctgacac tgtctaggcg                                         20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
cttagaaccc tccagtttaa                                         20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
aggaaacaca cgtgtaatta                                         20
```

```
<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
ggaggacaga aactccatgc                                                  20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
tgttctcaga taaaaggatg                                                  20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
agaccttgtc aaagatggat                                                  20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
agattgcatt aaatctccac                                                  20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
catgggtaga ttttcaata                                                   20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
catttgcact cctgggtatg                                                  20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide
```

-continued

<400> SEQUENCE: 147
tagatttcag gtgtggcata                                                    20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
tctccacaag ttcagcaaac                                                    20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
aaagctcctc aaaggttttg                                                    20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
cccgcctcct tgcttttact                                                    20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
gaggagtaca acaccacgga                                                    20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
tgagaagctt taggcgggcg                                                    20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
gtcccacagc tgcagggagg                                                    20

<210> SEQ ID NO 154
<211> LENGTH: 20

-continued

```
<212> TYPE: DNA
<213> ORGANISM: Artificial Sequence
<220> FEATURE:
<223> OTHER INFORMATION: Antisense Oligonucleotide

<400> SEQUENCE: 154
cctggctgat caactttcat                                          20
```

ANTISENSE INHIBITION OF VASCULAR ENDOTHELIAL GROWTH FACTOR RECEPTOR-1 EXPRESSION

FIELD OF THE INVENTION

The present invention provides compositions and methods for modulating the expression of vascular endothelial growth factor receptor-1. In particular, this invention relates to compounds, particularly oligonucleotides, specifically hybridizable with nucleic acids encoding vascular endothelial growth factor receptor-1. Such compounds have been shown to modulate the expression of vascular endothelial growth factor receptor-1.

BACKGROUND OF THE INVENTION

As a mitogen that acts primarily on endothelial cells, vascular endothelial growth factor (VEGF, or VEGF-A) is essential for endothelial cell differentiation (vasculogenesis) and for the sprouting of new capillaries from pre-existing vessels (angiogenesis) during embryonic development and wound repair. Signaling by VEGF affects a number of biological functions, including endothelial cell survival via inhibition of apoptosis, cell proliferation, vascular permeability, monocyte activation, chemotaxis, and cell migration. Thus, VEGF is believed to play a key role in wound healing, postnatal angiogenesis during pregnancy, and in human pathophysiological conditions such as cancer, rheumatoid arthritis, ocular neovascular disorders, and cardiovascular disease (Zachary and Gliki, *Cardiovasc. Res.,* 2001, 49, 568–581).

For transmission of the VEGF signal, VEGF binds to three receptor protein tyrosine kinases, vascular endothelial growth factor receptors-1, -2, and -3, that are structurally related to the PDGF family of class III receptors, characterized by cytoplasmic regions with an insert sequence within the catalytic domain, a single transmembrane domain, and seven immunoglobulin-like extracellular domains. Monomeric vascular endothelial growth factor receptors have 100-fold less affinity for VEGF, and thus, ligands preferentially bind to predimerized receptors. Upon ligand binding, the receptors auto- or trans-phosphorylate specific cytoplasmic tyrosine residues to initiate an intracellular cascade of signaling that ultimately reaches nuclear transcription factor effectors (Zachary and Gliki, *Cardiovasc. Res.,* 2001, 49, 568–581).

Most biological functions of VEGF are mediated through vascular endothelial growth factor receptor-2, and the role of vascular endothelial growth factor receptor-1 is currently less well understood (Zachary and Gliki, *Cardiovasc. Res.,* 2001, 49, 568–581).

Vascular endothelial growth factor receptor-1 (also known as VEGF receptor-1, VEGFR1, fms-related tyrosine kinase 1, Flt-1, FLT1, oncogene flt, and vascular endothelial growth factor/vascular permeability factor receptor) binds VEGF with highest affinity, but also binds VEGF-B (an alternative splice form of VEGF), and the closely related placenta growth factor (PlGF) with weaker affinities (Shibuya, *Int. J. Biochem. Cell Biol.,* 2001, 33, 409–420).

The human vascular endothelial growth factor receptor-1 gene was originally isolated from a human placenta DNA library (Shibuya et al., *Oncogene,* 1990, 5, 519–524) and its physical map location was confirmed when a yeast artificial chromosome (YAC) from human chromosomal band 13q12, bearing the closely linked FLT1 and FLT3 genes, was isolated and characterized (Imbert et al., *Cytogenet. Cell. Genet.,* 1994, 67, 175–177).

Expression of VEGF receptor-1 was once believed to restricted to proliferating endothelial cells, but expression of both VEGF receptor-1 and VEGF receptor-2 has been demonstrated more recently in atherosclerotic lesions and in several non-endothelial tumor cell types (Epstein et al., *Cardiovasc. Res.,* 2001, 49, 532–542). For example, co-expression of both receptors with VEGF is found in melanoma cells derived from primary and metastatic lesions (Graeven et al., *J. Cancer Res. Clin. Oncol.,* 1999, 125, 621–629).

Vascular endothelial growth factor receptor-1 was also found to be expressed in human peripheral blood monocytes and stimulates tissue factor production and chemotaxis, mediating monocyte recruitment and procoagulant activity (Clauss et al., *J. Biol. Chem.,* 1996, 271, 17629–17634). Expression of both VEGF-B and vascular endothelial growth factor receptor-1 is significantly upregulated renal clear cell carcinomas (Gunningham et al., *Cancer Res.,* 2001, 61, 3206–3211), and expression of vascular endothelial growth factor receptor-1 is also significantly higher in breast carcinoma as compared to normal breast (Gunningham et al., *J. Pathol.,* 2001, 193, 325–332).

Kaposi sarcoma (KS) is the most common tumor associated with HIV-1 infection, developing in nearly 30% of all cases. Characteristics of these KS tumors are abnormal vascularization and the proliferation of endothelial cells and spindle (tumor) cells. Vascular endothelial growth factor receptor-1 is expressed at high levels in AIDS-KS cell lines, while normal skin cells from the same patients did not express vascular endothelial growth factor receptor-1, suggesting that vascular endothelial growth factor receptor-1 plays a role in the development and progression of KS (Masood et al., *Proc. Natl. Acad. Sci. U.S.A.,* 1997, 94, 979–984).

Domain deletion studies of vascular endothelial growth factor receptor-1 have been performed, and it was determined that only two of the immunoglobulin-like extracellular domains of vascular endothelial growth factor receptor-1 are necessary and sufficient for binding VEGF with near-native affinity. The crystal structure of a complex between domain 2 of vascular endothelial growth factor receptor-1 and VEGF has been determined at 1.7-angstrom resolution (Wiesmann et al., *Cell,* 1997, 91, 695–704).

Vascular endothelial growth factor receptor-1 has a dual function in angiogenesis, acting as a positive or negative regulatory factor in different biological conditions. Under pathological conditions, such as when tumor-forming murine Lewis lung carcinoma (LLC) cells overexpressing placenta growth factor-2 (a ligand specific for vascular endothelial growth factor receptor-1) are injected into mice, vascular endothelial growth factor receptor-1 acts as a positive signal transducer and angiogenesis is induced, stimulating tumor growth. When the same LLC cells are overexpressing VEGF and are injected into mice, there is no increase in tumor growth rate (Hiratsuka et al., *Cancer Res.,* 2001, 61, 1207–1213).

Vascular endothelial growth factor receptor-1 can also act as a negative regulator of vascular endothelial growth factor receptor-2. Differential splicing of the vascular endothelial growth factor receptor-1 transcript results in a full-length receptor and a naturally occurring, soluble form of the extracellular domain of vascular endothelial growth factor receptor-1 (sVEGFR-1 or sFLT-1). This sFLT-1 isoform can form heterodimers with vascular endothelial growth factor receptor-2 (Kendall et al., *Biochem. Biophys. Res. Commun.,* 1996, 226, 324–328), and when overexpressed, sFLT-1 but not an artificial, soluble vascular endothelial growth factor receptor-2, can act as a receptor antagonist and inhibit VEGF-induced cell proliferation and migration of human microvascular endothelial cells and human umbilical vein endothelial cells (HUVECs) by forming and inactive complex with VEGF and with full length vascular endothelial growth factor receptor-2 (Roeckl et al., *Exp. Cell Res.*, 1998, 241, 161–170; Zachary and Gliki, *Cardiovasc. Res.*, 2001, 49, 568–581). By influencing the availability of VEGF and placental growth factor-2, sFLT-1 acts as an antagonist to VEGF action and is believed to play a pivotal role in generation of placental vascular diseases like pre-eclampsia or intrauterine growth retardation (Hornig et al., *Lab. Invest.*, 2000, 80, 443–454).

Because sFLT-1 has a strong affinity for VEGF, it has also been tested as a VEGF-blocking reagent in experimental animal models for carcinogenesis and shown to be effective in the suppression of solid tumor growth (Goldman et al., *Proc. Natl. Acad. Sci. U.S.A.*, 1998, 95, 8795–8800).

Disclosed and claimed in U.S. Pat. No. 5,861,484 are naturally occurring or recombinantly engineered soluble VEGF receptor-related inhibitor proteins comprising truncated and modified forms of vascular endothelial growth factor receptor-1 as well as a composition comprising said inhibitors and a pharmaceutically acceptable carrier (Kendall and Thomas, 1999).

Disclosed and claimed in PCT Publication WO 00/75319 are nucleic acid constructs encoding chimeric fusions of VEGF receptor-1 and VEGF receptor-2 polypeptide sequences, having improved pharmacokinetic properties, as well as methods of making and using said chimeric polypeptides to decrease or inhibit plasma leakage and/or vascular permeability in a mammal (Papadopoulos. Nicholas et al., 2000).

Disclosed and claimed in U.S. Pat. No. 5,830,880 is a recombinant DNA construct for the prophylaxis or therapy of tumor diseases, which comprises an activator sequence, a cell cycle regulated promoter module, and a DNA sequence encoding an anti-tumor substance, wherein the activator sequence is a promoter for vascular endothelial growth factor receptor-1(Sedlacek et al., 1998).

Mouse embryos deficient in vascular endothelial growth factor receptor-1 possess mature, differentiated endothelial cells, but assemble these cells into large, abnormal, disorganized vascular channels, and die in utero at mid-somite stages (Fong et al., *Nature*, 1995, 376, 66–70). It was later determined that the primary defect in these vascular endothelial growth factor receptor-1 null mice was an increase in the number of hemangioblasts (endothelial progenitor cells), due to an alteration in cell fate determination among mesenchymal cells, and the formation of disorganized vascular channels was a secondary phenotype resulting from overcrowding of the endothelial cell population. Thus, vascular endothelial growth factor receptor-1 regulates commitment to the hemangioblast cell fate during development (Fong et al., *Development*, 1999, 126, 3015–3025).

The modulation of vascular endothelial growth factor receptor-1 activity and/or expression is an ideal target for therapeutic intervention aimed at regulating the VEGF signaling pathway in the prevention and treatment of cancer, cardiovascular disease, ocular neovascular disorders such as diabetic retinopathy, and rheumatoid arthritis.

In addition to its mitogenic effects, VEGF has been observed in increased levels in the brain after an ischemic event, and is predicted to have a neuroprotective effect against glutamate toxicity. When an antisense oligonucleotide targeting vascular endothelial growth factor receptor-1 was used to inhibit its expression in hippocampal neurons, it was concluded that there are two independent anti-apoptotic pathways in adult brain mediated by VEGF receptors-1 and -2, but that the neuroprotective effect is not mediated by vascular endothelial growth factor receptor-1 (Matsuzaki et al., *Faseb J.*, 2001, 12, 12).

Two phosphorothioate antisense oligonucleotides, both 18 nucleotides in length, complementary to bovine vascular endothelial growth factor receptor-1, were used to inhibit gene expression and show that the mitogenic, chemotatic, and platelet activating factor-stimulating activities of VEGF on bovine aortic endothelial cells were not dependent on vascular endothelial growth factor receptor-1 but required the activation of vascular endothelial growth factor receptor-2 (Bernatchez et al., *J. Biol. Chem.*, 1999, 274, 31047–31054).

Capillaries are composed of endothelial cells and pericytes, with the latter cell type encircling the former. Hypoxia, the principal cause of angiogenesis in adult tissues, induces the proliferation of both pericytes and endothelial cells. A phosphorothioate antisense oligonucleotide, 17 nucleotides in length, complementary to human vascular endothelial growth factor receptor-1 and spanning a region from 7 bases upstream to 10 bases downstream of the translation initiation codon, was used to inhibit expression of vascular endothelial growth factor receptor-1 and show that the hypoxia-induced stimulation of pericyte growth is mediated by vascular endothelial growth factor receptor-1 (Yamagishi et al., *Lab. Invest.*, 1999, 79, 501–509).

Disclosed and claimed in U.S. Pat. No. 5,916,763 are nucleic acid sequences for a vascular endothelial growth factor receptor-1 promoter, expression vectors and recombinant host cells containing this promoter and an antisense RNA corresponding to a gene encoding a VEGF receptor, as well as methods for screening drugs that regulate the transcriptional activity of the vascular endothelial growth factor receptor-1 promoter and methods for endothelial-specific gene expression and treatment of disease, particularly by inhibiting angiogenesis (Williams and Morishita, 1999).

Disclosed and claimed in PCT Publication WO 98/07851 are nucleic acid molecules substantially free of natural contaminants wherein the sequences are homologous to the antisense strand of the non-translated 3' end of the vascular endothelial growth factor receptor-1 gene, and the molecules are designed to prevent the activity of the promoter elements in the vascular endothelial growth factor receptor-1 gene (Bergmann and Preddie, 1998).

Investigative strategies aimed at studying vascular endothelial growth factor receptor-1 localization and function have involved the use of specific antibodies directed against a peptide fragment from the extracellular domain of vascular endothelial growth factor receptor-1, as well as the use of antisense oligonucleotides, transgenic animals, soluble and truncated forms of vascular endothelial growth factor receptor-1, and chimeric fusion proteins.

Currently, there are no known therapeutic agents that effectively inhibit the synthesis and/or function of vascular endothelial growth factor receptor-1. Consequently, there remains a long felt need for agents capable of effectively inhibiting vascular endothelial growth factor receptor-1 function.

Antisense technology is emerging as an effective means for reducing the expression of specific gene products and therefore may prove to be uniquely useful in a number of therapeutic, diagnostic, and research applications for the modulation of vascular endothelial growth factor receptor-1 expression.

The present invention provides compositions and methods for modulating vascular endothelial growth factor receptor-1 expression, including modulation of the alternatively spliced sFLT-1 isoform of vascular endothelial growth factor receptor-1.

SUMMARY OF THE INVENTION

The present invention is directed to compounds, particularly antisense oligonucleotides, which are targeted to a nucleic acid encoding vascular endothelial growth factor receptor-1, and which modulate the expression of vascular endothelial growth factor receptor-1. Pharmaceutical and other compositions comprising the compounds of the invention are also provided. Further provided are methods of modulating the expression of vascular endothelial growth factor receptor-1 in cells or tissues comprising contacting said cells or tissues with one or more of the antisense compounds or compositions of the invention. Further provided are methods of treating an animal, particularly a human, suspected of having or being prone to a disease or condition associated with expression of vascular endothelial growth factor receptor-1 by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding vascular endothelial growth factor receptor-1, ultimately modulating the amount of vascular endothelial growth factor receptor-1 produced. This is accomplished by providing antisense compounds which specifically hybridize with one or more nucleic acids encoding vascular endothelial growth factor receptor-1. As used herein, the terms "target nucleic acid" and "nucleic acid encoding vascular endothelial growth factor receptor-1" encompass DNA encoding vascular endothelial growth factor receptor-1, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of vascular endothelial growth factor receptor-1. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding vascular endothelial growth factor receptor-1. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding vascular endothelial growth factor receptor-1, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U.S.A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'–5' linkages, 2'–5' linked analogs of these, and those having inverted polarity wherein one or more internucleotide linkages is a 3' to 3', 5' to 5' or 2'to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—,—$CH_2$—N ($CH_3$)—O—$CH_2$— [known as a methylene (methylimino) or MMI backbone], —$CH_2$—O—N($CH_3$)—$CH_2$—, —$CH_2$—N($CH_3$)—N ($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$ and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2' $OCH_2CH_2OCH_3$, also known as 2'—O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'—O-dimethylaminoethoxyethyl or 2'-DMAEOE), i.e., 2'—O—$CH_2$—O—$CH_2$—$N(CH_2)_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'—O—$CH_3$), 2'-aminopropoxy (2'—$OCH_2CH_2CH_2NH_2$), 2'-allyl (2'—$CH_2$—CH=$CH_2$), 2'—O-allyl (2'—O—$CH_2$—CH=$CH_2$) and 2'-fluoro (2'—F). The 2'-modification may be in the arabino (up) position or ribo (down) position. A preferred 2'-arabino modification is 2'—F. Similar modifications may also be made at other positions on the oligonucleotide, particularly the 3' position of the sugar on the 3' terminal nucleotide or in 2 '–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5, 4-b][1,4]benzoxazin-2 (3H)-one), carbazole cytidine (2H-pyrimido[4,5-b]indol-2-one), pyridoindole cytidine (H-pyrimido[3',2':4,5]pyrrolo[2, 3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds.,*Antisense Research and Applications*, CRC Press, Boca Raton, 1993, pp. 276–278) and are presently preferred base substitutions, even more particularly when combined with 2'—O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluores-ceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA,* 1989, 86, 6553–6556), cholic acid (Manoharan et al., *Bioorg. Med. Chem. Let.,* 1994, 4, 1053–1060), a thioether, e.g., hexyl-S-tritylthiol (Manoharan et al.,*Ann. N.Y. Acad. Sci.,* 1992, 660, 306–309; Manoharan et al., *Bioorg. Med. Chem. Let.,* 1993, 3, 2765–2770), a thiocholesterol (Oberhauser et al., *Nucl. Acids Res.,* 1992, 20, 533–538), an aliphatic chain, e.g., dodecandiol or undecyl residues (Saison-Behmoaras et al., *EMBO J.,* 1991, 10, 1111–1118; Kabanov et al., *FEBS Lett.,* 1990, 259, 327–330; Svinarchuk et al., *Biochimie,* 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651–3654; Shea et al., *Nucl. Acids Res.,* 1990, 18, 3777–3783), a polyamine or a polyethylene glycol chain (Manoharan et al., *Nucleosides & Nucleotides,* 1995, 14, 969–973), or adamantane acetic acid (Manoharan et al., *Tetrahedron Lett.,* 1995, 36, 3651–3654), a palmityl moiety (Mishra et al., *Biochim. Biophys. Acta,* 1995, 1264, 229–237), or an octadecylamine or hexylamino-carbonyl-oxycholesterol moiety (Crooke et al., *J. Pharmacol. Exp. Ther.,* 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459, 127; 5,521,291; 5,543,158; 5,547,932; 5,583,020; 5,591, 721; 4,426,330; 4,534,899; 5,013,556; 5,108,921; 5,213, 804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of vascular endothelial growth factor receptor-1 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding vascular endothelial growth factor receptor-1, enabling sandwich and other assays to easily be constructed to exploit this fact. Hybridization of the antisense oligonucleotides of the invention with a nucleic acid encoding vascular endothelial growth factor receptor-1 can be detected by means known in the art. Such means may include conjugation of an enzyme to the oligonucleotide, radiolabelling of the oligonucleotide or any other suitable detection means. Kits using such detection means for detecting the level of vascular endothelial growth factor receptor-1 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'—O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24, 25-dihydro-fusidate, sodium glycodihydrofusidate. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. Ser. Nos. applications 08/886,829 (filed Jul. 1, 1997), 09/108,673 (filed Jul. 1, 1998), 09/256,515 (filed Feb. 23, 1999), 09/082,624 (filed May 21, 1998) and 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms,* Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.,* 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release,* 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting,* 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research,* 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P. Pharma. Sci.,* 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters,* 1987, 223, 42; Wu et al., *Cancer Research,* 1993, 53, 3765).

Various liposomes comprising one or more glycolipids are known in the art. Papahadjopoulos et al. (*Ann. N.Y. Acad. Sci.,* 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.,* 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.,* 1980, 53, 2778) described liposomes comprising a nonionic detergent, $2C_{12}15G$, that contains a PEG moiety. Illum et al. (*FEBS Lett.,* 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., *J. Pharm. Pharmacol.*, 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: Remington's Pharmaceutical Sciences, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc.

Sterling Va.). Other 2'—O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research,* 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.,* 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'—O-(2-Methoxyethyl) Modified Amidites

2'—O-Methoxyethyl-substituted nucleoside amidites are prepared as follows, or alternatively, as per the methods of Martin, P., *Helvetica Chimica Acta,* 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'—O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'—O-Methoxyethyl-5'—O-dimethoxytrityl-5-methyluridine

2'—O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'—O-Acetyl-2'—O-methoxyethyl-5'—O-dimethoxytrityl-5-methyluridine

2'—O-Methoxyethyl-5'—O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'—O-Acetyl-2'—O-methoxyethyl-5'—O-dimethoxytrityl-5-methyl-4-triazoleuridine

A first solution was prepared by dissolving 3'—O-acetyl-2'—O-methoxyethyl-5'—O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'—O-Methoxyethyl-5'—O-dimethoxytrityl-5-methylcytidine

A solution of 3'—O-acetyl-2'—O-methoxyethyl-5'—O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'—O-methoxyethyl-5'—O-dimethoxytrityl-5-methylcytidine

2'—O-Methoxyethyl-5'—O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-Benzoyl-2'—O-methoxyethyl-5'—O-dimethoxytrityl-5-methylcytidine-3'-amidite

N4-Benzoyl-2'—O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'—O-(Aminooxyethyl) Nucleoside Amidites and 2'—O-(dimethylaminooxyethyl) Nucleoside Amidites 2'-(Dimethylaminooxyethoxy) Nucleoside Amidites 2'-(Dimethylaminooxyethoxy) nucleoside amidites [also known in the art as 2'—O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'—O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'—O-tert-Butyldiphenylsilyl-2'—O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'—O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'—O-([2-phthalimidoxy)ethyl]-5'-t-butyldiphenylsilyl-5-methyluridine

5'—O-tert-Butyldiphenylsilyl-2'—O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'—O-([2-phthalimidoxy)ethyl]-5'-t-butyldiphenylsilyl-5-methyluridine as white foam (21.819 g, 86%).

5'—O-tert-butyldiphenylsilyl-2'—O-[(2-formadoximinooxy)ethyl]-5-methyluridine

2'—O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at –10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'—O-(aminooxyethyl) thymidine, which was then dissolved in MeOH (67.5 mL). To this formaldehyde (20% aqueous solution, w/w, 1.1 eq.) was added and the resulting mixture was strirred for 1 h. Solvent was removed under vacuum; residue chromatographed to get 5'—O-tert-butyldiphenylsilyl-2'—O-[(2-formadoximinooxy) ethyl]-5-methyluridine as white foam (1.95 g, 78%).

5'—O-tert-Butyldiphenylsilyl-2'—O-[N,N-dimethylaminooxyethyl]-5-methyluridine

5'—O-tert-butyldiphenylsilyl-2'—O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1 M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated dryness. The residue obtained was purified by flash column chromatography and eluted with 5% MeOH in $CH_2Cl_2$ to get 5'—O-tert-butyldiphenylsilyl-2'—O-[N,N-dimethylaminooxyethyl]-5-methyluridine as a white foam (14.6 g, 80%).

2'—O-(dimnethylamuinooxyethyl)-5-methyluridine

Triethylamine trihydrofluoride (3.9 mL, 24.0 mmol) was dissolved in dry THF and triethylamine (1.67 mL, 12 mmol, dry, kept over KOH). This mixture of triethylamine-2HF was then added to 5'—O-tert-butyldiphenylsilyl-2'—O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MEOH in $CH_2Cl_2$ to get 2'—O-(dimethylaminooxyethyl)-5-methyluridine (766 mg, 92.5%).

5'—O-DMT-2'—O-(dimethylaminooxyethyl)-5-methyluridine

2'—O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'—O-DMT-2'-O-(dimethylamino-oxyethyl)-5-methyluridine (1.13 g, 80%).

5'—O-DMT-2'—O-(2-N,N-dimethylaminooxyethyl)-5-methyluridine-3'-[(2-cyancethyl)-N,N-diisopropylphosphoramidite]

5'—O-DMT-2'—O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'—O-DMT-2'—O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'—O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'—O-(2-ethylacetyl)-5'—O-(4,4'-dimethoxytrityl)guanosine-3'-[(2-cyanoethyl)-N,N-diisopropylphosphoramidite]

The 2'—O-aminooxyethyl guanosine analog may be obtained by selective 2'—O-alkylation of diaminopurine riboside. Multigram quantities of diaminopurine riboside may be purchased from Schering AG (Berlin) to provide 2'—O-(2-ethylacetyl) diaminopurine riboside along with a minor amount of the 3'—O-isomer. 2'—O-(2-ethylacetyl) diaminopurine riboside may be resolved and converted to 2'—O-(2-ethylacetyl)guanosine by treatment with adenosine deaminase. (McGee, D. P. C., Cook, P. D., Guinosso, C. J., WO 94/02501 A1 940203.) Standard protection procedures should afford 2'—O-(2-ethylacetyl)-5'—O-(4,4'-dimethoxytrityl)guanosine and 2-N-isobutyryl-6-O-diphenylcarbamoyl-2'—O-(2-ethylacetyl)-5'—O-(4,4'-dimethoxytrityl)guanosine which may be reduced to provide 2-N-isobutyryl-6-O-diphenylcarbamoyl-2'—O-(2-hydroxyethyl)-5'—O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'—O-([2-phthalmidoxy]ethyl)-5'—O-(4,4'-dimethoxytrityl) guanosine-3'-[(2-cyanoethyl)-N,N-diisopropylphosphoramidite].

2'-dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'—O—CH$_2$—O—CH$_2$—N(CH$_2$)$_2$, or 2'-DMAEOE nucleoside amidites) are prepared as follows. Other nucleoside amidites are prepared similarly.

2'—O-[2(2-N,N-dimethylaminoethoxy)ethyl]-5-methyl Uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. O$^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'—O-dimethoxytrityl-2'—O-[2(2-N,N-dimethylaminoethoxy) ethyl)]-5-methyl Uridine To 0.5 g (1.3 mmol) of 2'—O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with CH$_2$Cl$_2$ (2×200 mL). The combined CH$_2$Cl$_2$ layers are washed with saturated NaHCO$_3$ solution, followed by saturated NaCl solution and dried over anhydrous sodium sulfate. Evaporation of the solvent followed by silica gel chromatography using MeOH:CH$_2$Cl$_2$:Et$_3$N (20:1, v/v, with 1% triethylamine) gives the title compound.

5'—O-Dimethoxytrityl-2'—O-[2(2-N,N-dimethylaminoethoxy)-ethyl)]-5-methyl Uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'—O-dimethoxytrityl-2'—O-[2(2-N,N-dimethylaminoethoxy)ethyl)]-5-methyluridine (2.17 g, 3 mmol) dissolved in CH$_2$Cl$_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or U.S. Pat. No. 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. No. 5,130,302 and 5,177,198, both herein incorporated by reference.

Example 3

Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry,* 1996, 4,5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'—O-Me]-[2'-deoxy]-[2'—O-Me]Chimeric Phosphorothioate Oligonucleotides

Chimeric oligonucleotides having 2'—O-alkyl phosphorothioate and 2'-deoxy phosphorothioate oligo-nucleotide segments are synthesized using an Applied Biosystems automated DNA synthesizer Model 380B, as above. Oligonucleotides are synthesized using the automated synthesizer and 2'-deoxy-5'-dimethoxytrityl-3'—O-phosphor-amidite for the DNA portion and 5'-dimethoxytrityl-2'—O-methyl-3'—O-phosphoramidite for 5' and 3' wings. The standard synthesis cycle is modified by increasing the wait step after the delivery of tetrazole and base to 600 s repeated four times for RNA and twice for 2'—O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'—O-(2-Methoxyethyl)]-[2'-deoxy]-[2'—O-(Methoxyethyl)]Chimeric Phosphorothioate Oligonucleotides

[2'—O-(2-methoxyethyl)]-[2'-deoxy]-[-2'—O-(methoxyethyl)]chimeric phosphorothioate oligonucleotides were prepared as per the procedure above for the 2'—O-methyl chimeric oligonucleotide, with the substitution of 2'—O-(methoxyethyl) amidites for the 2'—O-methyl amidites.

[2'—O-(2-Methoxyethyl)Phosphodiester]-[2'-deoxy Phosphorothioate]-[2'—O-(2-Methoxyethyl) Phosphodiester]Chimeric Oligonucleotides

[2'-O-(2-methoxyethyl phosphodiester]-[2'-deoxy phosphorothioate]-[2'—O-(methoxyethyl)phosphodiester] chimeric oligonucleotides are prepared as per the above procedure for the 2'—O-methyl chimeric oligonucleotide with the substitution of 2'—O-(methoxyethyl) amidites for the 2'—O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 6 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

HuVEC Cells

The human umbilical vein endothilial cell line HuVEC was obtained from the American Type Culure Collection (Manassas, Va). HuVEC cells were routinely cultured in EBM (Clonetics Corporation Walkersville, Md.) supplemented with SingleQuots supplements (Clonetics Corporation, Walkersville, Md.). Cells were routinely passaged by trypsinization and dilution when they reached 90% confluence were maintained for up to 15 passages. Cells were seeded into 96-well plates (Falcon-Primaria #3872) at a density of 10000 cells/well for use in RT-PCR analysis.

For Northern blotting or other analyses, cells may be seeded onto 100 mm or other standard tissue culture plates and treated similarly, using appropriate volumes of medium and oligonucleotide.

b.END Cells

The mouse brain endothelial cell line b.END was obtained from Dr. Werner Risau at the Max Plank Instititute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds

When cells reached 80% confluency, they were treated with oligonucleotide. For cells grown in 96-well plates, wells were washed once with 200 $\mu$L OPTI-MEM™-1 reduced-serum medium (Gibco BRL) and then treated with 130 $\mu$L of OPTI-MEDM™-1 containing 3.75 $\mu$g/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'—O-methoxyethyl gapmer (2'—O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'—O-methoxyethyl gapmer (2'—O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Vascular Endothelial Growth Factor Receptor-1 Expression Antisense modulation of vascular endothelial growth factor receptor-1 expression can be assayed in a variety of ways known in the art. For example, vascular endothelial growth factor receptor-1 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of vascular endothelial growth factor receptor-1 can be quantitated in a variety of ways well known in the art, such as immunoprecipitation, Western blot analysis (immunoblotting), ELISA or fluorescence-activated cell sorting (FACS). Antibodies directed to vascular endothelial growth factor receptor-1 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+mRNA Isolation

Poly(A)+mRNA was isolated according to Miura et al., *Clin. Chem.*, 1996, 42, 1758–1764. Other methods for poly(A)+mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Vascular Endothelial Growth Factor Receptor-1 mRNA Levels Quantitation of vascular endothelial growth factor receptor-1 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 μL PCR cocktail (1×TAQMAN™ buffer A, 5.5 mM MgCl$_2$, 300 μM each of DATP, dCTP and dGTP, 600 μM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 μL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 μL of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human vascular endothelial growth factor receptor-1 were designed to hybridize to a human vascular endothelial growth factor receptor-1 sequence, using published sequence information (GenBank accession number NM_002019, incorporated herein as SEQ ID NO:3). For human vascular endothelial growth factor receptor-1 the PCR primers were:

```
forward primer:   CCCTCGCCGGAAGTTGTA              (SEQ ID NO: 4)

reverse primer:   ATAATTAACGAGTAGCCACGAGTCAA      (SEQ ID NO: 5)

and the PCR probe was: FAM-ACCTGCGACTGAGAAATCTGCTCGCT-TAMRA  (SEQ ID NO: 6)
``` where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were:

```
forward primer:   GAAGGTGAAGGTCGGAGTC             (SEQ ID NO: 7)

reverse primer:   GAAGATGGTGATGGGATTTC            (SEQ ID NO: 8)

and the PCR probe was: 5' JOE-CAAGCTTCCCGTTCTCAGCC- TAMRA 3'  (SEQ ID NO: 9)
``` where JOE (PE-Applied Biosystems, Foster City, Calif.) is the fluorescent reporter dye) and TAMRA (PE-Applied Biosystems, Foster City, Calif.) is the quencher dye.

Probes and primers to mouse vascular endothelial growth factor receptor-1 were designed to hybridize to a mouse vascular endothelial growth factor receptor-1 sequence, using published sequence information (GenBank accession number L07297, incorporated herein as SEQ ID NO:10). For mouse vascular endothelial growth factor receptor-1 the PCR primers were:

| | | |
|---|---|---|
| forward primer: | CAATGTGGAGAAGCCGAGACAA | (SEQ ID NO: 11) |
| reverse primer: | GAGGTGTTGAAAGACTGGAACGA | (SEQ ID NO: 12) | and the PCR probe was: FAM-ACACCTGTCGCGTGAAGAGTGGGTC-TAMRA  (SEQ ID NO: 13)

where FAM (PE-Applied Biosystems, Foster City, Calif.) is the fluorescent reporter dye) and TAMRA (PE-Applied Biosystems, Foster City, Calif.) is the quencher dye. For mouse GAPDH the PCR primers were:

| | | |
|---|---|---|
| forward primer: | GGCAAATTCAACGGCAGAGT | (SEQ ID NO: 14) |
| reverse primer: | GGGTCTCGCTCCTGGAAGAT | (SEQ ID NO: 15) | and the PCR probe was: 5' JOE-AAGGCCGAGAATGGGAAGCTTGTCATC- TAMRA 3'  (SEQ ID NO: 16)

where JOE (PE-Applied Biosystems, Foster City, Calif.) is the fluorescent reporter dye) and TAMPA (PE-Applied Biosystems, Foster City, Calif.) is the quencher dye.

Example 14

Northern Blot Analysis of Vascular Endothelial Growth Factor Receptor-1 mRNA Levels Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human vascular endothelial growth factor receptor-1, a human vascular endothelial growth factor receptor-1 specific probe was prepared by PCR using the forward primer CCCTCGCCGGAAGTTGTA (SEQ ID NO: 4) and the reverse primer ATAATTAACGAGTAGCCAC-GAGTCAA (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

To detect mouse vascular endothelial growth factor receptor-1, a mouse vascular endothelial growth factor receptor-1 specific probe was prepared by PCR using the forward primer CAATGTGGAGAGCCGAGACAA (SEQ ID NO:11) and the reverse primer GAGGTGTTGAAA-GACTGGAACGA (SEQ ID NO: 12). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Vascular Endothelial Growth Factor Receptor-1 Expression by Chimeric Phosphorothioate Oligonucleotides having 2'-MOE Wings and a Deoxy Gap In accordance with the present invention, a series of oligonucleotides were designed to target different regions of the human vascular endothelial growth factor receptor-1 RNA, using published sequences (GenBank accession number NM_002019, incorporated herein as SEQ ID NO: 3, GenBank accession number D64016, incorporated herein as SEQ ID NO: 17, GenBank accession number D00133, incorporated herein as SEQ ID NO: 18, GenBank accession number U01134, incorporated herein as SEQ ID NO: 19, GenBank accession number AI188382, the complement of which is incorporated herein as SEQ ID NO: 20, and GenBank accession number S77812, incorporated herein as SEQ ID NO: 21). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human vascular endothelial growth factor receptor-1 mRNA levels by quantitative real-time PCR as described in other examples herein. Data are averages from two experiments. If present, "N.D." indicates "no data".

TABLE 1

Inhibition of human vascular endothelial growth factor receptor-1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 142624 | Start Codon | 3 | 239 | gctgaccatggtgagcgcga | 89 | 22 |
| 142625 | Coding | 3 | 326 | aggatcttttaattttgaac | 35 | 23 |
| 142626 | Coding | 3 | 346 | gtgccttttaaactcagttc | 85 | 24 |
| 142627 | Coding | 3 | 352 | tgctgggtgccttttaaact | 84 | 25 |
| 142628 | Coding | 3 | 530 | gttttgcttgagctgtgttca | 90 | 26 |
| 142629 | Coding | 3 | 585 | ccttcttctttgaagtaggt | 80 | 27 |
| 142630 | Coding | 3 | 636 | cgaaaggtctacctgtatca | 91 | 28 |
| 142631 | Coding | 3 | 814 | gatatgatgaagccctttct | 88 | 29 |
| 142632 | Coding | 3 | 862 | actgttgcttcacaggtcag | 92 | 30 |
| 142633 | Coding | 3 | 991 | gcagtacaattgaggacaag | 91 | 31 |
| 142634 | Coding | 3 | 1083 | tttggtcaattcgtcgcctt | 88 | 32 |
| 142635 | Coding | 3 | 1165 | cgacaagtataaagtccttt | 84 | 33 |
| 142636 | Coding | 3 | 1195 | acagatttgaatgatggtcc | 89 | 34 |
| 142637 | Coding | 3 | 1236 | cagtgatgaatgcttatca | 92 | 35 |
| 142638 | Coding | 3 | 1408 | ttgataattaacgagtagcc | 91 | 36 |
| 142639 | Coding | 3 | 1464 | actgttttatgctcagcaag | 94 | 37 |
| 142640 | Coding | 3 | 1486 | gtgaggttttttaaacacatt | 69 | 38 |
| 142641 | Coding | 3 | 1494 | gagtggcagtgaggttttta | 76 | 39 |
| 142642 | Coding | 3 | 1502 | gacaattagagtggcagtga | 86 | 40 |
| 142643 | Coding | 3 | 1510 | ttcacattgacaattagagt | 87 | 41 |
| 142644 | Coding | 3 | 1574 | gctgcccagtgggtagagag | 78 | 42 |
| 142645 | Coding | 3 | 1580 | ttgtctgctgcccagtgggt | 83 | 43 |
| 142646 | Coding | 3 | 1628 | ccacttgattgtaggttgag | 80 | 44 |
| 142647 | Coding | 3 | 1723 | atgttgctgtcagcatccag | 82 | 45 |
| 142648 | Coding | 3 | 1745 | gatgctctcaattctgtttc | 82 | 46 |
| 142649 | Coding | 3 | 1757 | catgcgctgagtgatgctct | 0 | 47 |
| 142650 | Coding | 3 | 1855 | ccaactttattggaagctat | 90 | 48 |
| 142651 | Coding | 3 | 1956 | acagtttcaggtcctctcct | 73 | 49 |
| 142652 | Coding | 3 | 2009 | ccgcagtaaaatccaagtaa | 89 | 50 |
| 142653 | Coding | 3 | 2051 | ttgcttgctaatactgtagt | 74 | 51 |
| 142654 | Coding | 3 | 2143 | gctctgcaggcataggtgcc | 62 | 52 |
| 142655 | Coding | 3 | 2149 | ttcctggctctgcaggcata | 87 | 53 |
| 142656 | Coding | 3 | 2165 | ttcccctgtgtatacattcc | 86 | 54 |
| 142657 | Coding | 3 | 2177 | ctggaggatttcttcccctg | 88 | 55 |
| 142658 | Coding | 3 | 2365 | cctggtcctaaaataattcc | 48 | 56 |
| 142659 | Coding | 3 | 2389 | ctttcaataaacagcgtgct | 46 | 57 |
| 142660 | Coding | 3 | 2395 | gtgactctttcaataaacag | 48 | 58 |
| 142661 | Coding | 3 | 2403 | cctctctgtgactctttca | 61 | 59 |
| 142662 | Coding | 3 | 2692 | tcccacttgctggcatcata | 64 | 60 |
| 142663 | Coding | 3 | 2698 | gcaaactcccacttgctggc | 57 | 61 |
| 142664 | Coding | 3 | 2787 | gtgatttcttaatgccaaat | 49 | 62 |
| 142665 | Coding | 3 | 2812 | ttcacagccacagtccggca | 78 | 63 |
| 142666 | Coding | 3 | 2860 | gtcatcagagctttgtactc | 51 | 64 |
| 142667 | Coding | 3 | 2933 | ttgcttggtgcaggctccca | 82 | 65 |
| 142668 | Coding | 3 | 2941 | ggccctccttgcttggtgca | 39 | 66 |
| 142669 | Coding | 3 | 2947 | atcagaggccctccttgctt | 47 | 67 |
| 142670 | Coding | 3 | 2953 | atcaccatcagaggccctcc | 73 | 68 |
| 142671 | Coding | 3 | 3002 | tttgctcttgaggtagttgg | 37 | 69 |
| 142672 | Coding | 3 | 3008 | gtcacgtttgctcttgaggt | 54 | 70 |
| 142673 | Coding | 3 | 3013 | aataagtcacgtttgctctt | 52 | 71 |
| 142674 | Coding | 3 | 3262 | tccatgcctctgccacttg | 76 | 72 |
| 142675 | Coding | 3 | 3292 | cgatgaatgcactttctgga | 57 | 73 |
| 142676 | Coding | 3 | 3299 | caggtcccgatgaatgcact | 53 | 74 |
| 142677 | Coding | 3 | 3306 | tcgctgccaggtcccgatga | 86 | 75 |
| 142678 | Coding | 3 | 3313 | atgtttctcgctgccaggtc | 56 | 76 |
| 142679 | Coding | 3 | 3379 | ttcttataaatatcccgggc | 15 | 77 |
| 142680 | Coding | 3 | 3439 | gattcgggagccatccattt | 47 | 78 |
| 142681 | Coding | 3 | 3737 | gtagtctttaccatcctgtt | 55 | 79 |
| 142682 | Coding | 3 | 3742 | gggatgtagtctttaccatc | 22 | 80 |
| 142683 | Coding | 3 | 3905 | gattctttccaggctcatga | 59 | 81 |
| 142684 | Coding | 3 | 3911 | ggttttgattctttccaggc | 41 | 82 |
| 142685 | Coding | 3 | 3949 | tcaaacatggaggtgcatt | 51 | 83 |
| 142686 | Stop Codon | 3 | 4255 | gtcaaactctagatgggtgg | 42 | 84 |
| 142687 | 3'UTR | 3 | 4420 | ttacattcttgttagtcaaa | 43 | 85 |
| 142688 | 3'UTR | 3 | 5739 | ttgcataaatagcatcaaac | 44 | 86 |
| 142689 | 3'UTR | 3 | 6117 | agtcttccacaaaagccgct | 52 | 87 |
| 142690 | 3'UTR | 3 | 6905 | atgaggctagcgagtatctg | 48 | 88 |
| 142691 | 5'UTR | 17 | 357 | cagggcacttgaactttatt | 29 | 89 |
| 142692 | Intron | 17 | 1699 | gcagcggccccaagcgtgcc | 61 | 90 |
| 142693 | Intron | 18 | 149 | gagcctctctacaaatacag | 45 | 91 |
| 142694 | Coding | 19 | 2235 | tccgagagaaaacagccttt | 62 | 92 |
| 142695 | 3'UTR | 19 | 2323 | gagacaactgttacttttta | 50 | 93 |
| 142696 | 3'UTR | 19 | 2384 | gggaggagcatctcctccga | 27 | 94 |
| 142697 | 3'UTR | 19 | 2468 | agcagcccccctcggcctgaa | 64 | 95 |
| 142698 | 3'UTR | 19 | 2600 | ttggcatcaaaatggaaagg | 55 | 96 |
| 142699 | Exon | 20 | 203 | tggtgatgatgacgatgacg | 49 | 97 |
| 142700 | Exon | 20 | 519 | caccatgcccggctaatttt | 78 | 98 |
| 142701 | Stop Codon | 21 | 195 | ccgatgaggtagagttctat | 60 | 99 |

As shown in Table 1, SEQ ID NOs 22, 24, 25, 26, 27, 28, 29, 30, 31, 32, 33, 34, 35, 36, 37, 38, 39, 40, 41, 42, 43, 44, 45, 46, 48, 49, 50, 51, 52, 53, 54, 55, 56, 57, 58, 59, 60, 61, 62, 63, 64, 65, 67, 68, 70, 71, 72, 73, 74, 75, 76, 78, 79, 81, 83, 87, 88, 90, 91, 92, 93, 95, 96, 97, 98 and 99 demonstrated at least 45% inhibition of human vascular endothelial growth factor receptor-1 expression in this assay and are therefore preferred. The target sites to which these preferred sequences are complementary are herein referred to as "active sites" and are therefore preferred sites for targeting by compounds of the present invention.

Example 16

Antisense Inhibition of Mouse Vascular Endothelial Growth Receptor-1 Expression by Chimeric Phosphorothioate Cleotides having 2'-MOE Wings and a Deoxy Gap In accordance with the present invention, a second series of oligonucleotides were designed to target different regions of the mouse vascular endothelial growth factor receptor-1RNA, using published sequences (GenBank accession number L07297, incorporated herein as SEQ ID NO: 10, GenBank accession number D88690, incorporated herein as SEQ ID NO: 100, and GenBank accession number AJ224863, incorporated herein as SEQ ID NO: 101). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse vascular endothelial growth factor receptor-1 mRNA levels by quantitative real-time PCR as described in other examples herein. Data are averages from two experiments. If present, "N.D." indicates "no data".

TABLE 2

Inhibition of mouse vascular endothelial growth factor receptor-1 mRNA levels by chimeric phosphorothioate oligonucleotides having 2'-MOE wings and a deoxy gap

| ISIS # | REGION | TARGET SEQ ID NO | GET SITE | TARGET SEQUENCE | % INHIB | SEQ ID NO |
|---|---|---|---|---|---|---|
| 142626 | Coding | 10 | 123 | gtgccttttaaactcagttc | 74 | 24 |
| 142627 | Coding | 10 | 129 | tgctgggtgccttttaaact | 94 | 25 |
| 142641 | Coding | 10 | 1274 | gagtggcagtgaggttttta | 19 | 39 |
| 142648 | Coding | 10 | 1525 | gatgctctcaattctgtttc | 94 | 46 |
| 142651 | Coding | 10 | 1736 | acagtttcaggtcctctcct | 90 | 49 |
| 142658 | Coding | 10 | 2145 | cctggtcctaaaataattcc | 68 | 56 |
| 142659 | Coding | 10 | 2169 | ctttcaataaacagcgtgct | 61 | 57 |
| 142660 | Coding | 10 | 2175 | gtgactctttcaataaacag | 69 | 58 |
| 142662 | Coding | 10 | 2472 | tcccacttgctggcatcata | 87 | 60 |
| 142663 | Coding | 10 | 2478 | gcaaactcccacttgctggc | 84 | 61 |
| 142664 | Coding | 10 | 2567 | gtgatttcttaatgccaaat | 68 | 62 |
| 142665 | Coding | 10 | 2592 | ttcacagccacagtccggca | 78 | 63 |
| 142666 | Coding | 10 | 2640 | gtcatcagagcttttgtactc | 67 | 64 |
| 142669 | Coding | 10 | 2727 | atcagaggccctccttgctt | 83 | 67 |
| 142670 | Coding | 10 | 2733 | atcaccatcagaggccctcc | 85 | 68 |
| 142671 | Coding | 10 | 2782 | tttgctcttgaggtagttgg | 76 | 69 |
| 142673 | Coding | 10 | 2793 | aataagtcacgttttgctctt | 65 | 71 |
| 142674 | Coding | 10 | 3039 | tccatgcctctgccacttg | 83 | 72 |
| 142675 | Coding | 10 | 3069 | cgatgaatgcactttctgga | 20 | 73 |
| 142677 | Coding | 10 | 3083 | tcgctgccaggtcccgatga | 88 | 75 |
| 142678 | Coding | 10 | 3090 | atgttttctcgctgccaggtc | 72 | 76 |
| 142679 | Coding | 10 | 3156 | ttcttataaatatcccgggc | 6 | 77 |
| 142683 | Coding | 10 | 3682 | gattctttccaggctcatga | 77 | 81 |
| 142684 | Coding | 10 | 3688 | ggttttgattctttccaggc | 74 | 82 |
| 142687 | 3'UTR | 10 | 4171 | ttacattcttgttagtcaaa | 61 | 85 |
| 142961 | Start Codon | 10 | 18 | cagctgaccatggtgagcaa | 94 | 102 |
| 142962 | Coding | 10 | 73 | tcctgtgagaagcagacacc | 90 | 103 |
| 142963 | Coding | 10 | 169 | tctgcacttgagaaagagag | 84 | 104 |
| 142964 | Coding | 10 | 321 | aggcccgtgtggttggcctg | 86 | 105 |
| 142965 | 5'UTR | 101 | 395 | agccaaaaccatctataact | 23 | 106 |
| 142966 | Coding | 10 | 413 | aaggactccctgcatcacta | 91 | 107 |
| 142967 | Coding | 10 | 587 | taaagcctctcctactgtcc | 96 | 108 |
| 142968 | Coding | 10 | 605 | acgttgcatttgctattata | 89 | 109 |
| 142969 | 5'UTR | 101 | 682 | accaagacacacaacgtgga | 39 | 110 |
| 142970 | Coding | 10 | 692 | tattggtctgccgatgggtc | 88 | 111 |
| 142971 | Coding | 10 | 710 | tttggacatctaggattgta | 9 | 112 |
| 142972 | 5'UTR | 101 | 802 | ttctaagaggtctgctcagc | 69 | 113 |
| 142973 | Coding | 10 | 834 | ctcttagttgctttaccagg | 93 | 114 |
| 142974 | Coding | 10 | 1098 | gggaaggccttcactttcat | 93 | 115 |
| 142975 | Coding | 10 | 1369 | agtgaggacttgtctgctgc | 93 | 116 |
| 142976 | Coding | 10 | 1391 | gagggatgccatacacggtg | 47 | 117 |
| 142977 | 5'UTR | 101 | 1476 | actgactcgaatgttcttgg | 12 | 118 |
| 142978 | Coding | 10 | 1592 | gagagtcagccaccaccaat | 91 | 119 |
| 142979 | Coding | 10 | 1772 | taatgtctctgtacaggaat | 86 | 120 |
| 142980 | Coding | 10 | 1878 | atgacaaggttcagagtgat | 72 | 121 |
| 142981 | Coding | 10 | 1945 | ttccctgtgtatatgttcc | 90 | 122 |
| 142982 | 5'UTR | 101 | 1959 | tcctagggaagctggccgcg | 53 | 123 |
| 142983 | Coding | 10 | 2016 | tcactgaggttttgaagcag | 75 | 124 |
| 142984 | Coding | 10 | 2097 | ttgaaccaagtgatctgagg | 67 | 125 |
| 142985 | Coding | 10 | 2160 | aacagcgtgctgtttcctgg | 73 | 126 |
| 142986 | Coding | 10 | 2216 | ggttggtggctcggcaccta | 88 | 127 |
| 142987 | Coding | 100 | 2272 | acaatcattcctcctgcttt | 86 | 128 |
| 142988 | Coding | 10 | 2275 | tgacttgtctgaggttcctt | 56 | 129 |
| 142989 | Coding | 10 | 2340 | gttagaaggagccaaaagag | 63 | 130 |
| 142990 | Coding | 10 | 2382 | tttacttcggaagaagaccg | 75 | 131 |
| 142991 | 3'UTR | 100 | 2407 | atgtccaaactcattttggg | 80 | 132 |
| 142992 | Coding | 10 | 2577 | cggcaggtgggtgatttctt | 81 | 133 |
| 142993 | 3'UTR | 100 | 2639 | cagcttcacaacttaaaaat | 79 | 134 |
| 142994 | Coding | 10 | 2670 | tggccgatgtgggtcaagat | 76 | 135 |
| 142995 | 3'UTR | 100 | 2819 | gttatccaggaactatttac | 84 | 136 |
| 142996 | 3'UTR | 100 | 2834 | taagcattataacttgttat | 79 | 137 |
| 142997 | Coding | 10 | 2895 | ctgctgacactgtctaggcg | 77 | 138 |
| 142998 | 3'UTR | 100 | 2913 | cttagaaccctccagtttaa | 82 | 139 |
| 142999 | 3'UTR | 100 | 3043 | aggaaacacacgtgtaatta | 82 | 140 |
| 143000 | Coding | 10 | 3052 | ggaggacagaaatccatgc | 72 | 141 |
| 143001 | Coding | 10 | 3107 | tgttctcagataaaaggatg | 60 | 142 |
| 143002 | Coding | 10 | 3233 | agaccttgtcaaagatggat | 68 | 143 |

TABLE 2-continued

Inhibition of mouse vascular endothelial growth factor receptor-1 mRNA levels by chimeric phosphorothioate oligonucleotides having 2'-MOE wings and a deoxy gap

| ISIS # | REGION | TARGET SEQ ID NO | GET SITE | TARGET SEQUENCE | % INHIB | SEQ ID NO |
|---|---|---|---|---|---|---|
| 143003 | 3'UTR | 100 | 3252 | agattgcattaaatctccac | 73 | 144 |
| 143004 | 3'UTR | 100 | 3282 | catgggtagattttcaata | 85 | 145 |
| 143005 | Coding | 10 | 3322 | catttgcactcctgggtatg | 81 | 146 |
| 143006 | Coding | 10 | 3396 | tagatttcaggtgtggcata | 72 | 147 |
| 143007 | Coding | 10 | 3464 | tctccacaagttcagcaaac | 47 | 148 |
| 143008 | Coding | 10 | 3701 | aaagctcctcaaaggttttg | 81 | 149 |
| 143009 | Coding | 10 | 3855 | cccgcctccttgcttttact | 80 | 150 |
| 143010 | Coding | 10 | 3996 | gaggagtacaacaccacgga | 75 | 151 |
| 143011 | Stop Codon | 10 | 4018 | tgagaagctttaggcgggcg | 68 | 152 |
| 143012 | 3'UTR | 10 | 4320 | gtcccacagctgcagggagg | 67 | 153 |
| 143013 | 3'UTR | 10 | 6036 | cctggctgatcaactttcat | 80 | 154 |

As shown in Table 2, SEQ ID NOs 24, 25, 46, 49, 56, 57, 58, 60, 61, 62, 63, 64, 67, 68, 69, 71, 72, 75, 76, 81, 82, 85, 102, 103, 104, 105, 107, 108, 109, 111, 113, 114, 115, 116, 119, 120, 121, 122, 124, 125, 126, 127, 128, 130, 131, 132, 133, 134, 135, 136, 137, 138, 139, 140, 141, 142, 143, 144, 145, 146, 147, 149, 150, 151, 152, 153 and 154 demonstrated at least 60% inhibition of mouse vascular endothelial growth factor receptor-1 expression in this experiment and are therefore preferred. The target sites to which these preferred sequences are complementary are herein referred to as "active sites" and are therefore preferred sites for targeting by compounds of the present invention.

Example 17

Western Blot Analysis of Vascular Endothelial Growth Factor Receptor-1 Protein Levels Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to vascular endothelial growth factor receptor-1 is used, with a radio-labelled or fluorescently labeled secondary antibody directed against the primary antibody species. Bands are visualized using a PHOSPHORIMAGER™ (Molecular Dynamics, Sunnyvale Calif.).

What is claimed is:

1. An antisense compound consisting of SEQ ID NO: 55 or 42.

* * * * *